United States Patent [19]

Oku et al.

[11] Patent Number: 4,963,536
[45] Date of Patent: Oct. 16, 1990

[54] DIPHOSPHONIC ACID COMPOUNDS, AND PHARMACEUTICAL COMPOSITION COMPRISING THE SAME USEFUL FOR TREATING BONE DISEASES

[75] Inventors: Teruo Oku; Eishiro Todo; Chiyoshi Kasahara, all of Sakuramura; Katsuya Nakamura, Yatabemachi; Hiroshi Kayakiri, Sakuramura; Masashi Hashimoto, Sakuramura; all of Japan

[73] Assignee: Fujisawa Pharmaceutical Company, Ltd., Osaka, Japan

[21] Appl. No.: 333,953

[22] Filed: Apr. 6, 1989

Related U.S. Application Data

[62] Division of Ser. No. 42,444, Apr. 24, 1987, Pat. No. 4,857,513.

[30] Foreign Application Priority Data

Apr. 24, 1986 [GB] United Kingdom ................. 8610019
Aug. 5, 1986 [GB] United Kingdom ................. 8619074
Mar. 6, 1987 [GB] United Kingdom ................. 8705347

[51] Int. Cl.$^5$ .......................... C07F 9/58; C07F 9/60; C07F 9/6506; A61K 31/685
[52] U.S. Cl. ......................... 514/76; 514/82; 514/89; 514/94; 514/95; 514/96; 514/107; 546/22; 546/23; 548/113; 548/119; 549/6; 562/13
[58] Field of Search ..................... 260/502.5 C, 501.12; 546/22, 23; 548/113, 119; 549/6; 562/13; 514/89, 82, 94, 95, 96, 76, 107

[56] References Cited

U.S. PATENT DOCUMENTS

4,876,248 10/1989 Breliere et al. ..................... 514/108

*Primary Examiner*—Alan L. Rotman
*Attorney, Agent, or Firm*—Oblon, Spivak, McClelland, Maier & Neustadt

[57] ABSTRACT

A compound of the formula:

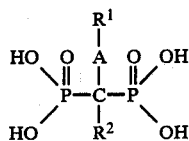

wherein
$R^1$-A- is a group of the formula:

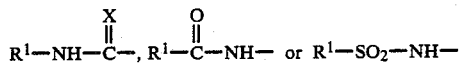

in which
$R^1$ is aryl or a heterocyclic group, each of which may be substituted with substituent(s) selected from the group consisting of lower alkyl, lower alkoxy, lower alkylthio, halo(lower)alkyl, acyl, acylamino and halogen, or lower alkyl which may be substituted with a heterocyclic group optionally substituted with acyl, and
X is O or S, and
$R^2$ is hydrogen or lower alkyl, provided that when $R^1$ is lower alkyl, then
$R^1$-A- is a group of the formula:

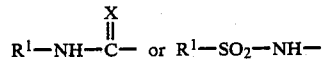

in which
$R^1$ and X are each as defined above, processes for the preparation thereof and pharmaceutical composition comprising the same.

3 Claims, No Drawings

DIPHOSPHONIC ACID COMPOUNDS, AND PHARMACEUTICAL COMPOSITION COMPRISING THE SAME USEFUL FOR TREATING BONE DISEASES

This is a division, of application Ser. No. 07/042,444, filed on Apr. 24, 1987, U.S. Pat. No. 4,857,513.

This invention relates to new diphosphonic acid compounds and pharmaceutically acceptable salts thereof.

More particularly, it relates to new diphosphonic acid compounds and pharmaceutically acceptable salts thereof which have inhibitory activities on bone resorption, to processes for the preparation thereof, to a pharmaceutical composition comprising the same and to a method for the treatment of bone diseases characterized by abnormal bone metabolism in human being or animals.

One object of this invention is to provide new and useful diphosphonic acid compounds and pharmaceutically acceptable salts thereof which possess inhibitory activities on bone resorption.

Another object of this invention is to provide processes for the preparation of said diphosphonic acid compounds and salts thereof.

A further object of this invention is to provide a pharmaceutical composition comprising, as an active ingredient, said diphosphonic acid compounds and pharmaceutically acceptable salts thereof.

Still further object of this invention is to provide a therapeutical method for the treatment of bone diseases characterized by abnormal bone metabolism such as osteoporosis, Paget's bone disease, osteolysis, hypercalcemia of malignancy and rheumatoid arthritis.

It has been known as described in U.S. Pat. No. 3,906,062 that some of the alkyl ester derivatives of the object compounds as stated below have pesticidal activity. However, it has never been known that they have inhibitory activities on bone resorption.

It has been known as described in German Patent Application publication No. 2741513 that some acylaminoalkylidenediphosphonic acid compounds are useful as a polishing agent in dentifrice preparations. However, it has never been known that they have inhibitory activities on bone resorption.

Some diphosphonic acid compounds having antiinflammatory and antirheumatic activities have been known as described in European Patent Application publication No. 100718.

Some diphosphonic acid compounds which are useful for the treatment of bone diseases have been known as described in European Patent Application publication No. 170228.

The object diphosphonic acid compounds of this invention are new and can be represented by the following general formula [I]:

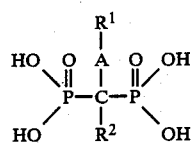

wherein
R¹-A- is a group of the formula:

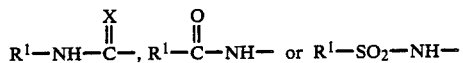

in which
R¹ is aryl or a heterocyclic group, each of which may be substituted with substituent(s) selected from the group consisting of lower alkyl, lower alkoxy, lower alkylthio, halo(lower)alkyl, acyl, acylamino and halogen, or lower alkyl which may be substituted with a heterocyclic group optionally substituted with acyl, and
X is O or S, and
R² is hydrogen or lower alkyl, provided that when R¹ is lower alkyl, then
R¹-A- is a group of the formula:

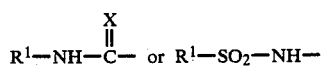

in which R¹ and X are each as defined above.

The object compound [I] or its salt can be prepared by processes as illustrated in the following reaction schemes.

Process 1

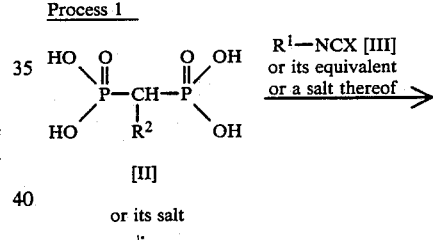

[II]

or its salt

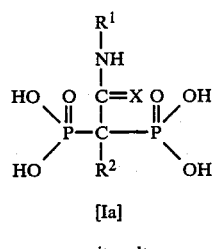

[Ia]

or its salt

Process 2

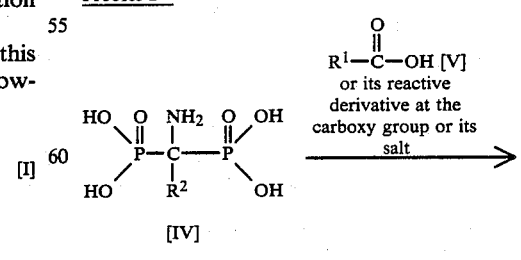

[IV]

or its reactive derivative at the amino group or its salt

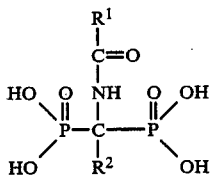

[Ib]

or its salt

Process 3

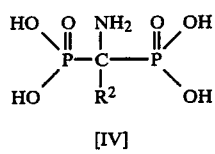

[IV]

or its reactive
derivative at the
amino group
or its salt

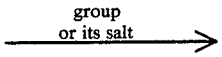

R¹—SO₂—OH [VI]
or its reactive
derivative
at the sulfo
group
or its salt

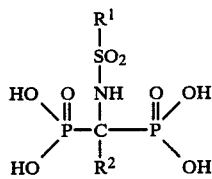

[Ic]

or its salt

Process 4

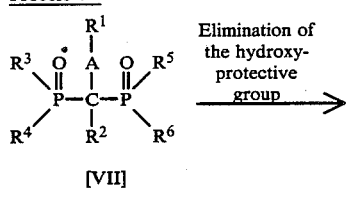

[VII]

or its salt

Elimination of
the hydroxy-
protective
group

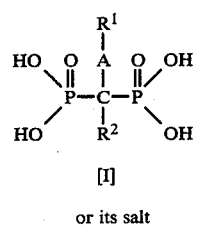

[I]

or its salt wherein $R^3$, $R^4$, $R^5$ and $R^6$ are each protected hydroxy, and $R^1$, $R^2$, A and X are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "aryl" may be phenyl, naphthyl, tolyl, mesityl, cumenyl, and the like, preferably phenyl, naphthyl and lower alkyl [e.g. methyl, ethyl, propyl, isopropyl, butyl, isobutyl, pentyl, hexyl, etc.] substituted phenyl.

Suitable "heterocyclic group" may include saturated or unsaturated, monocyclic or polycyclic one containing at least one hetero atom such as nitrogen atom, oxygen atom or sulfur atom.

The preferred examples of thus defined "heterocyclic group" may be unsaturated, 3 to 8-membered, more preferably 5 or 6-membered heteromonocyclic group containing 1 to 4-nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

unsaturated, condensed heterocyclic group containing 1 to 5 nitrogen atom(s), for example, indolyl, isoindolyl, indolizinyl, benzimidazolyl, quinolyl, isoquinolyl, indazolyl, benzotriazolyl, etc.;

unsaturated, 3 to 8-membered heteromonocyclic group containing 1 to 2 oxygen atom(s) and 1 to 3 nitrogen atom(s), for example, oxazolyl, isoxazolyl, oxadiazolyl, etc.;

saturated, 3 to 8-membered heteromonocyclic group containing 1 to 2 oxygen atom(s) and 1 to 3 nitrogen atom(s), for example, morpholino, sydnonyl, etc.;

unsaturated, condensed heterocyclic group containing 1 to 2 oxygen atom(s) and 1 to 3 nitrogen atom(s), for example, benzoxazolyl, benzoxadiazolyl, etc.;

unsaturated, 3 to 8-membered heteromonocyclic group containing 1 to 2 sulfur atom(s) and 1 to 3 nitrogen atom(s), for example, thiazolyl, isothiazolyl, thiadiazolyl, etc.;

unsaturated, 3 to 8-membered heteromonocyclic group containing 1 to 2 sulfur atom(s), for example, thienyl, etc.;

unsaturated, condensed heterocyclic group containing 1 to 2 sulfur atom(s) and 1 to 3 nitrogen atom(s), for example, benzothiazolyl, benzothiadiazolyl, etc.;

unsaturated, 3 to 8-membered heteromonocyclic group containing an oxygen atom, for example, furyl, etc.;

unsaturated, condensed heterocyclic group containing 1 to 2 sulfur atom(s), for example, benzothienyl, etc.;

unsaturated, condensed heterocyclic group containing 1 to 2 oxygen atom(s), for example, benzofuranyl, etc.; or the like.

The above-mentioned "aryl" and "heterocyclic group" may be substituted with one or more, preferably one to three, more preferably one or two substituent(s) selected from the group consisting of the aforesaid lower alkyl; lower alkoxy [e.g. methoxy, ethoxy, propoxy, isopropoxy, butoxy, pentyloxy, hexyloxy, etc.]; lower alkylthio[e.g. methylthio, ethylthio, propylthio, isopropylthio, butylthio, pentylthio, hexylthio, etc.]; halo(lower)alkyl, preferably mono-, di- or tri-(halo)lower alkyl [e.g. chloromethyl, bromomethyl, fluoromethyl, dichloromethyl, difluoromethyl, trifluoromethyl, 2-chloroethyl, 2-bromoethyl, 3-chloropropyl, etc.]; acyl such as lower alkanoyl [e.g. formyl, acetyl, propionyl, hexanoyl, pivaloyl, etc.], lower alkoxycarbonyl [e.g. methoxycarbonyl, ethoxycarbonyl, tert-butoxycarbonyl, tert-pentyloxycarbonyl, hexyloxycarbonyl, etc.], ar(lower)alkoxycarbonyl [e.g. benzyloxycarbonyl, etc.], lower alkylsulfonyl [e.g. mesyl, ethylsulfonyl, etc.], arylsulfonyl [e.g. phenylsulfonyl, tosyl, etc.], or the like; acylamino such as lower alkanoylamino [e.g. formylamino, acetylamino, propionylamino, etc.], lower alkylsulfonylamino [e.g.

mesylamino, ethylsulfonylamino, propylsulfonylamino, etc.] or the like; and halogen [e.g. fluoro, chloro, bromo, iodo, etc.].

Preferable example of "aryl or a heterocyclic group, each of which may be substituted with substituent(s) selected from the group consisting of lower alkyl, lower alkoxy, lower alkylthio, halo(lower)alkyl, acyl, acylamino and halogen" thus defined may be phenyl, naphthyl, mono or di or tri(lower)alkylphenyl [e.g. tolyl, ethylphenyl, propylphenyl, cumenyl, butylphenyl, xylyl, mesityl, etc.], mono or di or tri(lower)alkoxyphenyl [e.g. methoxyphenyl, ethoxyphenyl, propoxyphenyl, isopropoxyphenyl, butoxyphenyl, neopentyloxyphenyl, dimethoxyphenyl, etc.], mono or di or tri(lower)alkylthiophenyl [e.g. methylthiophenyl, ethylthiophenyl, propylthiophenyl, isopropylthiophenyl, butylthiophenyl, dimethylthiophenyl, etc.], mono or di or trihalophenyl [e.g. fluorophenyl, chlorophenyl, bromophenyl, iodophenyl, dichlorophenyl, (fluoro)chlorophenyl, diiodophenyl, difluorophenyl, trifluorophenyl, trichlorophenyl, etc.], mono or di or tri[halo(lower)alkyl]phenyl [e.g. chloromethylphenyl, dichloromethylphenyl, trifluoromethylphenyl, di(trifluoromethyl)phenyl, etc.], mono or di or triacylaminophenyl [e.g. mono or di or tri(lower)alkanoylaminophenyl (e.g. formylaminophenyl, acetylaminophenyl, propionylaminophenyl, di(acetylamino)phenyl, etc.), mono or di or tri(lower)alkylsulfonylaminophenyl (e.g. mesylaminophenyl, ethylsulfonylaminophenyl, propylsulfonylaminophenyl, di(mesylamino)phenyl, etc.), etc.], halogen and halo(lower)alkyl substituted phenyl [e.g. (chloro)trifluoromethylphenyl, (fluoro)trifluoromethylphenyl, di(chloro)chloromethylphenyl, etc.], lower alkoxy and halo(lower)alkyl substituted phenyl [e.g. (methoxy)trifluoromethylphenyl, (ethoxy)trifluoromethylphenyl, di(methoxy)chloromethylphenyl, etc.], pyridyl, mono or di or tri(lower)alkylpyridyl [e.g. methylpyridyl, ethylpyridyl, propylpyridyl, dimethylpyridyl, etc.], imidazolyl, imidazolyl substituted with acyl such as lower alkoxycarbonyl substituted imidazolyl [e.g. tert-butoxycarbonylimidazolyl, etc.] or the like, thienyl, quinolyl, benzo[b]thienyl, benzothiazolyl and mono or di or trihalobenzothiazolyl [e.g. chlorobenzothiazolyl, fluorobenzothiazolyl, etc.], in which more preferable one may be phenyl, mono($C_1$-$C_4$)alkylphenyl, mono($C_1$-$C_4$)alkoxyphenyl, mono($C_1$-$C_4$)alkylthiophenyl, mono or dihalophenyl, mono[halo($C_1$-$C_4$)alkyl]phenyl, mono($C_1$-$C_4$)alkanoylaminophenyl, mono($C_1$-$C_4$)alkylsulfonylaminophenyl, halogen and halo($C_1$-$C_4$)alkyl substituted phenyl, $C_1$-$C_4$ alkoxy and halo($C_1$-$C_4$)alkyl substituted phenyl, pyridyl, mono($C_1$-$C_4$)alkylpyridyl, imidazolyl, $C_1$-$C_4$ alkoxycarbonylimidazolyl, thienyl, quinolyl, benzo[b]thienyl, benzothiazolyl and monohalobenzothiazolyl, and most preferable ones are phenyl, tolyl, naphthyl, methoxyphenyl, methylthiophenyl, chlorophenyl, fluorophenyl, dichlorophenyl, trifluoromethylphenyl, acetylaminophenyl, mesylaminophenyl, (chloro)trifluoromethylphenyl, (methoxy)trifluoromethylphenyl, pyridyl, methylpyridyl, imidazolyl, tert-butoxycarbonylimidazolyl, thienyl, quinolyl, benzo[b]thienyl, benzothiazolyl and chlorobenzothiazolyl.

Suitable "lower alkyl" may be a straight or branched one such as methyl, ethyl, propyl, isopropyl, butyl, isobutyl, tert-butyl, pentyl, hexyl, and the like, in which more preferable one may be $C_1$-$C_4$ alkyl and the most preferable ones are methyl and butyl.

"Lower alkyl" group for $R^1$ may be substituted with the above-mentioned heterocyclic group which may be substituted with the above-mentioned acyl.

Suitable "protected hydroxy" may be hydroxy group protected by conventional protective group such as lower alkoxy [e.g. methoxy, ethoxy, propoxy, isopropoxy, butoxy, sec-butoxy, isobutoxy, tert-butoxy, pentyloxy, neopentyloxy, hexyloxy, etc.], optionally substituted ar(lower)alkoxy, for example, mono or di or triphenyl(lower)alkoxy which may be substituted with nitro [e.g. benzyloxy, 4-nitrobenzyloxy, benzhydryloxy, trityloxy, etc.], or the like, in which the preferable example may be lower alkoxy, more preferable one may be $C_1$-$C_4$alkoxy and the most preferable ones are ethoxy and isopropoxy.

Suitable pharmaceutically acceptable salts of the object compounds [I] are conventional non-toxic salts and include an inorganic base salt such as an alkali metal salt [e.g. sodium salt, potassium salt, etc.], an alkaline earth metal salt [e.g. calcium salt, magnesium salt, etc.] or an ammonium salt; an organic base salt such as an organic amine salt [e.g. methylamine salt, ethylamine salt, propylamine salt, isopropylamine salt, butylamine salt, tert-butylamine salt, dimethylamine salt, diethylamine salt, trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], or the like.

In this respect, it is to be noted the compounds [Ia] to [Ic] are included within the scope of the compounds [I], and accordingly the suitable salts of these compounds [Ia] to [Ic] are to be referred to those as exemplified for the object compounds [I] mentioned above.

The processes for preparing the object compounds [I] of the present invention are explained in detail in the following.

Process 1

The object compound [Ia] or its salt can be prepared by reacting a compound [II] or its salt with a compound [III] or its equivalent or a salt thereof.

Suitable salts of the compound [II] can be referred to the base salts as exemplified for the compound [I].

Suitable salts of the compound [III] can be referred to the acid addition salts as exemplified for the compound [I].

Suitable examples of equivalent of the compound [III] may include intermolecular condensed compounds of the compound [III] such as 3-(2-pyridyl)-3,4-dihydro-2H-pyrido[1,2-a]-1,3,5-triazine-2,4-dione prepared by subjecting 2-pyridylisothiocyanate to intermolecular condensation, etc.

This reaction is usually carried out in a solvent such as dioxane, tetrahydrofuran, benzene, chloroform, methylene chloride, N,N-dimethylformamide or any other organic solvent which does not adversely influence the reaction.

Further, this reaction can be carried out in the presence of a base such as an alkali metal [e.g. sodium, potassium, etc.], an alkaline earth metal [e.g. magnesium, calcium, etc.], the hydride or hydroxide thereof, alkali metal alkoxide [e.g. sodium methoxide, sodium ethoxide, potassium tert-butoxide, etc.], or the like.

The reaction temperature is not critical and the reaction is usually carried out under cooling to heating.

Process 2

The object compound [Ib] or its salt can be prepared by reacting a compound [IV] or its reactive derivative at the amino group or its salt with a compound [V] or its reactive derivative at the carboxy group or its salt.

Suitable reactive derivative at the amino group of the compound [IV] may include Schiff's base type imino or its tautomeric enamine type isomer formed by the reaction of the compound [IV] with a carbonyl compound such as aldehyde, ketone or the like; a silyl derivative formed by the reaction of the compound [IV] with a silyl compound such as bis(trimethylsilyl)acetamide, mono(trimethylsilyl)acetamide, bis(trimethylsilyl)urea or the like; a derivative formed by reaction of the compound [IV] with phosphorus trichloride or phosgene, and the like.

Suitable salts of the compound [IV] and its reactive derivative can be referred to the ones as exemplified for the compound [I].

Suitable reactive derivative at the carboxy group of the compound [V] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [V] to be used.

Suitable salts of the compound [V] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [V] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphoshate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metel bicarbonate, tri(lower)alkylamine, pyridine, di(lower)alkylaminopyridine, N-(lower)alkylmorpholine, N,N-di(lower)alkylbenzylamine, or the like. A liquid base can also be used as a solvent.

The reaction temperature is not critical, and the reaction is usually carried out under cooling to warming.

Process 3

The object compound [Ic] or its salt can be prepared by reacting a compound [IV] or its reactive derivative at the amino group or its salt with a compound [VI] or its reactive derivative at the sulfo group or its salt.

Suitable salts of the compound [VI] and its reactive derivative can be referred to the salts as exemplified for the compound [I].

This reaction can be carried out in substantially the same manner as Process 2, and therefore the reaction mode and reaction conditions [e.g. base, reactive derivative, condensing agent, solvent, reaction temperature, etc.] of this reaction are to be referred to those as explained in Process 2.

Process 4

The object compound [I] or its salt can be prepared by subjecting a compound [VII] or its salt to elimination reaction of the hydroxy-protective group.

This reaction is carried out in accordance with a conventional method such as hydrolysis, reduction or the like.

Suitable salts of the compound [VII] can be referred to the ones as exemplified for the compound [I].

The hydrolysis is preferably carried out in the presence of a base, an acid including Lewis acid, or halosilane compound.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g.

hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

Suitable halosilane compound may include halotri(-lower)alkylsilane [e.g. iodotrimethylsilane, bromotrimethylsilane, etc.], and the like.

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base, acid or halosilane compound can also be used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

The starting compound [VII], some of which are new, or its salt can be prepared by processes as illustrated in the following reaction schemes.

Process A

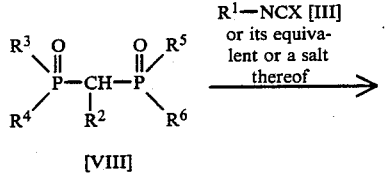

[VIII]

or its salt $R^1$—NCX [III]
or its equivalent or a salt thereof
⟶

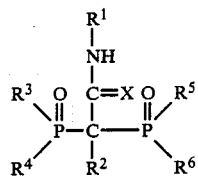

[VIIa]

or its salt

Process B

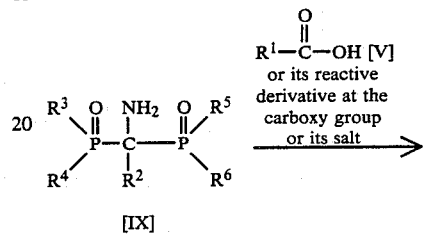

[IX]

or its reactive derivative at the amino group or its salt $R^1$—C(=O)—OH [V]
or its reactive derivative at the carboxy group or its salt
⟶

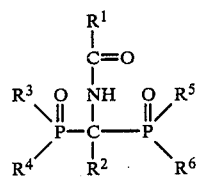

[VIIb]

or its salt

Process C

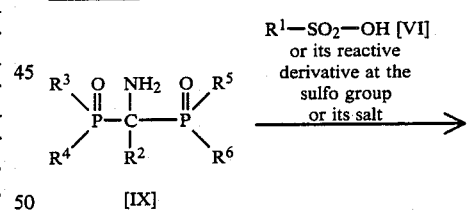

[IX]

or its reactive derivative at the amino group or its salt $R^1$—$SO_2$—OH [VI]
or its reactive derivative at the sulfo group or its salt
⟶

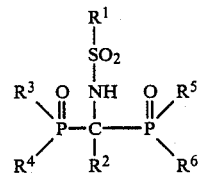

[VIIc]

or its salt

Process D

11

-continued

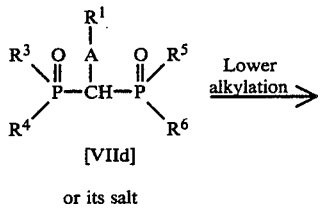
[VIId]

or its salt

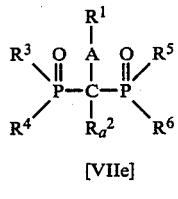
[VIIe]

or its salt wherein $R^2$ is lower alkyl and $R^1$, $R^2$, $R^3$, $R^4$, $R^5$, $R^6$, A and X are each as defined above.

The above-mentioned processes for preparing the starting compounds are explained in detail in the following.

Process A

The compound [VIIa] or its salt can be prepared by reacting a compound [VIII] or its salt with a compound [III] or its equivalent or a salt thereof.

Suitable salts of the compound [VIII] can be referred to the base salts as exemplified for the compound [I].

This reaction can be carried out in substantially the same manner as Process 1, and therefore the reaction mode and reaction conditions [e.g. base, solvent, reaction temperature, etc.] of this reaction are to be referred to those as explained in Process 1.

Process B

The compound [VIIb] or its salt can be prepared by reacting a compound [IX] or its reactive derivative at the amino group or its salt with a compound [V] or its reactive derivative at the carboxy group or its salt.

Suitable salts of the compound [IX] and its reactive derivative can be referred to the ones as exemplified for the compound [I].

This reaction can be carried out in substantially the same manner as Process 2, and therefore the reaction mode and reaction conditions [e.g. reactive derivative, condensing agent, solvent, reaction temperature, etc.] of this reaction are to be referred to those as explained in Process 2.

Process C

The compound [VIIc] or its salt can be prepared by reacting a compound [IX] or its reactive derivative at the amino group or its salt with a compound [VI] or its reactive derivative at the sulfo group or its salt.

This reaction can be carried out in substantially the same manner as Process 2, and therefore the reaction mode and reaction conditions [e.g. base, reactive derivative, condensing agent, solvent, reaction temperature, etc.] of this reaction are to be referred to those as explained in Process 2.

Process D

The compound [VIIe] or its salt can be prepared by reacting a compound [VIId] or its salt with a lower alkylating agent.

Suitable salts of the compound [VIId] can be referred to the ones as exemplified for the compound [I].

Suitable salts of the compound [VIIe] can be referred to the acid addition salt as exemplified for the compound [I].

Suitable lower alkylating agents may be lower alkyl halide [e.g. methyl iodide, ethyl iodide, propyl iodide, butyl iodide, etc.], lower alkyl arenesulfonate [e.g. methyl benzenesulfonate, ethyl tosylate, etc.], di(lower)alkyl sulfate [e.g. dimethyl sulfate, diethyl sulfate, etc.] or the like.

This reaction can be carried out in the presence of a base as exemplified in Process 1.

This reaction is usually carried out in a solvent such as dioxane, tetrahydrofuran, benzene, chloroform, methylene chloride, N,N-dimethylformamide or any other organic solvent which does not adversely influence the reaction, and in case that the above-mentioned lower alkylating agent is liquid, it can also be used as a solvent.

The reaction temperature is not critical, and the reaction is usually carried out under cooling to heating.

Both reactions of Process A and Process D can be carried out simultaneously, where a compound [III] and a lower alkylating agent are added to a compound [VIII] wherein $R^2$ is hydrogen to give a compound [VIIe]. This process is also included within the scope of the present invention.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compounds [I] and pharmaceutically acceptable salts thereof possess strong inhibitory activities on bone resorption, and useful for therapeutical treatment of bone diseases characterized by abnormal bone metabolism such as osteoporosis, Paget's bone disease, osteolysis, hypercalcemia of malignancy and rheumatoid arthritis.

For therapeutic purpose, the compounds [I] and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating said bone diseases. In general, amounts between 0.1 mg/body and about 1,000 mg/body may be administered per day.

In order to illustrate the usefulness of the object compound [I], the pharmacological test data of some representative compounds of the compound [I] are shown in the following.

Test method:

Neonatal calvaria were dissected aseptically from 1–2 day old rat (Wistar), washed in Dulbecco's modified eagle's medium and divided along the sagittal suture. The calvaria halves were pooled and randomized in the different groups. The calvaria halves were cultured separately as free-floating bones in multi-well dishes containing a 2 ml of Dulbecco's modified eagle's medium, with 10% heat-inactivated (56° C. for 1 hr) fetal calf serum. Treatment of hPTH(1-34)($1 \times 10^{-8}$M) and the Test Compound ($1 \times 10^{-7}$ or $1 \times 10^{-6}$M) was begun at zero time. All incubations were performed at 37° C., under an atmosphere of 95% air and 5% $CO_2$ for 6 days. Bone resorption was determined by measuring the accumulation of calcium in the medium at 6 days. The concentration of total calcium in culture medium was measured by OCPC method with a spectrophotometer (Hitachi model U-3200, Tokyo, Japan).

As comparative data, similar tests were conducted using culture medium with hPTH ($1 \times 10^{-8}$M) only, and culture medium without both hPTH and Test Compound.

Test results were represented in terms of percentage of inhibition calculated by the following formula:

$$\text{Inhibition (\%)} = \frac{C_P - C_D}{C_P - C_O} \times 100$$

$C_D$: the concentration of total calcium in culture medium treated with both hPTH and Test Compound $C_O$: the concentration of total calcium in control culture medium without both hPTH and Test Compound $C_P$: the concentration of total calcium in culture medium treated with hPTH only Test compounds:

(a) Tris(tert-butylamine)salt of [N-(phenyl)thiocarbamoylmethylene]bis(phosphonic acid)

(b) Tris(tert-butylamine)salt of [N-(4-chlorophenyl)carbamoylmethylene]bis(phosphonic acid)

(c) Tris(tert-butylamine)salt of [N-(4-chlorophenyl)thiocarbamoylmethylene]bis(phosphonic acid)

(d) Disodium salt of [N-(2-benzo[b]thienyl)thiocarbamoylmethylene]bis(phosphonic acid)

(e) Disodium salt of [N-(4-trifluoromethylphenyl)thiocarbamoylmethylene]bis(phosphonic acid)

(f) Disodium salt of [N-(3-trifluoromethylphenyl)thiocarbamoylmethylene]bis(phosphonic acid)

(g) Disodium salt of [N-(4-chloro-3-trifluoromethylphenyl)thiocarbamoylmethylene]bis(phosphonic acid)

(h) Disodium salt of [N-(4-methoxy-3trifluoromethylphenyl)thiocarbamoylmethylene]bis(phosphonic acid)

(i) Bis(tert-butylamine)salt of [(2-benzo[9 -thiophenecarboxamido)methylene]bis(phonic acid)

(j) Tris(tert-butylamine)salt of [(2-quinolinecerboxamido)methylene]bis(phosphonic acid)

(k) Disodium salt of [(4-chlorophenyl)sulfonylaminomethylene]bis(phosphonic acid)

(l) Disodium salt of [N-(3-mesylaminophenyl)-thiocarbamoylmethylene]bis(phosphonic acid)

| Test Compounds | Test Results Dose (M) | Inhibition (%) |
|---|---|---|
| (a) | $1 \times 10^{-7}$ | 54.3 |
|  | $1 \times 10^{-6}$ | 66.3 |
| (b) | $1 \times 10^{-7}$ | 46.6 |
|  | $1 \times 10^{-6}$ | 56.9 |
| (c) | $1 \times 10^{-6}$ | 57.0 |
| (d) | $1 \times 10^{-6}$ | 59.7 |
| (e) | $1 \times 10^{-6}$ | 65.9 |
| (f) | $1 \times 10^{-6}$ | 68.9 |
| (g) | $1 \times 10^{-6}$ | 112.4 |
| (h) | $1 \times 10^{-6}$ | 77.7 |
| (i) | $1 \times 10^{-7}$ | 45.0 |
| (j) | $1 \times 10^{-7}$ | 46.9 |
|  | $1 \times 10^{-6}$ | 53.8 |
| (k) | $1 \times 10^{-6}$ | 71.0 |
| (l) | $1 \times 10^{-6}$ | 52.4 |

The following Preparations and Examples are given for the purpose of illustrating the present invention in more detail.

Preparation 1

To a stirred solution of 2-aminobenzo[b]thiophene (1.11 g) in anhydrous toluene (4.5 ml) was added carbon disulfide (0.62 g) and triethylamine (0.755 g) successively. The solution was then stirred at 0°–5° C. for 3 days under nitrogen gas atmosphere. The precipitate was collected by filtration and was washed with anhydrous toluene (10 ml). The obtained white powder was dissolved in chloroform (4.5 ml), treated with triethylamine (0.76 g), and cooled to 0° C. To this solution was added dropwise ethyl chloroformate (0.84 g) over a period of 20 minutes. After being stirred at ambient temperature for one hour, the solution was washed twice with 1N hydrochloric acid (5 ml), and brine, and dried. The solvent was evaporated under reduced pressure and the residue was subjected to column chromatography on silica gel, eluted with n-hexane to give benzo[b]thiophene-2-isothiocyanate (118 mg) as an oil.

IR (Neat): 2080 $cm^{-1}$

NMR (CDCl$_3$, δ): 7.06 (1H, s), 7.32–7.41 (2H, m), 7.63–7.73 (2H, m)

Preparation 2

To a suspension of sodium hydride (120 mg, 60% oil dispersion) in distilled tetrahydrofuran (4 ml) was added tetraisopropyl methylenebis(phosphonate)(688 mg) in one portion at ambient temperature. After stirring for a few minutes, the mixture was allowed to cool in an ice bath and phenyl isothiocyanate (0.36 ml) was added thereto. The reaction mixture was stirred for 3 hours at ambient temperature and methanol (2 ml) was added to the reaction mixture to quench excess phenyl isothiocyanate. The mixture was concentrated under reduced pressure. The residue was dissolved in a mixture of diethyl ether and 1N hydrochloric acid. The separated organic layer was washed with water and dried over magnesium sulfate. The solvent was removed and the residue was subjected to column chromatography n silica gel using a mixture of chloroform and methanol (30:1 V/V) as an eluent to give tetraisopropyl [N-(phenyl)thiocarbamoylmethylene]bis(phosphonate) (0.75 g) as a crystal.

mp: 64°–66° C.

IR (Nujol): 3300, 1600, 1500, 1400, 1250, 1000 cm$^{-1}$

NMR (CDCl$_3$, δ): 1.2–1.6 (24H, m), 4.31 (1H, t, J=23.5 Hz), 4.65–5.0 (4H, m), 7.2–7.45 (3H, m), 7.75–7.85 (2H, m), 10.24 (1H, br s)

The following compounds (Preparations 3 to 27) were obtained according to a similar manner to that of Preparation 2.

Preparation 3

Tetraisopropyl [N-(4-fluorophenyl)carbamoylmethylene]bis-(phosphonate)
mp: 173°–174° C.
IR (Nujol): 3450, 3350, 1665 cm$^{-1}$ NMR (CDCl$_3$, δ): 1.26–1.50 (24H, m), 3.62
(1H, t, J=20 Hz), 4.69–4.97 (4H, m), 7.00 (2H, t, J=8 Hz), 7.48 (2H, dd, J=8 and 5 Hz), 7.56 (1H, s)

Preparation 4

Tetraisopropyl [N-(p-tolyl)carbamoylmethylene]bis-(phosphonate)
mp: 96°–98° C.
IR (Nujol): 3300, 1660 cm$^{-1}$
NMR (CDCl$_3$, δ): 1.20–1.52 (24H, m), 2.32 (3H, s), 3.53 (1H, t, J=20 Hz), 4.70–4.92 (4H, m), 7.12 (2H, d, J=8 Hz), 7.42 (2H, d, J=8 Hz), 8.69 (1H, s)

Preparation 5

Tetraisopropyl [N-(4-methoxyphenyl)carbamoylmethylene]-bis(phosphonate)
mp: 99°–100° C.
IR (Nujol) 3300, 1660 cm$^{-1}$
NMR (CDCl$_3$, δ): 1.31–1.41 (24H, m), 3.53 (1H, t, J=23 Hz), 3.79 (3H, s), 4.71–4.92 (4H, m), 6.86 (2H, d, J=9 Hz), 7.44 (2H, d, J=9 Hz), 8.65 (1H, s)

Preparation 6

Tetraisopropyl [N-(4-chlorophenyl)thiocarbamoylmethylene]bis(phosphonate)
NMR (CDCl$_3$, δ): 1.21–1.46 (24H, m), 4.30 (1H, t, J=22 Hz), 4.78 (4H, m), 7.35 and 7.78 (4H, ABq, J=8.8 Hz), 10.25 (1H, br s).

Preparation 7

Tetraisopropyl [N-(1-naphthyl)thiocarbamoylmethylene-]bis(phosphonate)
IR (Neat) : 3500, 3320, 2975, 2925, 1590, 1380, 1250, 1000 cm$^{-1}$
NMR (CDCl$_3$, δ): 1.37–1.47 (24H, m), 4.51 (1H, t, J=24 Hz), 4.90 (4H, m), 7.48–8.34 (7H, m), 10.30 (1H, br s)

Preparation 8

Tetraisopropyl [N-(3-trifluoromethylphenyl)-thiocarbamoylmethylene]bis(phosphonate)
mo:49°–51° C. IR (CH$_2$Cl$_2$): 2980, 2930, 1450, 1385, 1335, 1130, 990 cm$^{-1}$
NMR (CDCl$_3$, δ): 1.25–1.57 (24H, m), 4.34 (1H, t, J=23 Hz), 4.70–5.00 (4H, m), 7.50–7.60 (2H, m), 8.04 (1H, m), 8.16 (1H, s), 10.4 (1H, s)

Preparation 9

Tetraisopropyl [N-(4-trifluoromethylphenyl)-thiocarbamoylmethylene]bis(phosphonate)
mp: 98°–100° C.
IR (Nujol): 3250, 3200, 1610, 1320, 1250, 1120 cm$^{-1}$ NMR (CDCl$_3$, δ): 1.31–1.44 (24H, m), 4.32 (1H, t, J=23 Hz), 4.81 (4H, m), 7.66 and 8.00 (4H, ABq, J=8.5 Hz), 10.43 (1H, s)

Preparation 10

Tetraisopropyl [N-(3-chlorophenyl)thiocarbamoylmethylene]bis(phosphonate) mp: 61°–62° C.
IR (Neat): 3450, 3300, 1595, 1550, 1480, 1380, 1260, 1100, 1000 cm$^{-1}$
NMR (CDCl$_3$, δ): 1.21–1.44 (24H, m), 4.30 (1H, r, J=23 Hz), 4.69–4.91 (4H, m), 7.20–7.37 (2H, m), 7.65 (1H, br d, J=8 Hz), 8.00 (1H, br s), 10.27 (1H, s)

Preparation 11

Tetraisopropyl [N-(2-chlorophenyl)thiocarbamoylmethylene]bis(phosphonate)
IR (Neat): 3500, 3300, 1380, 1260, 990 cm$^{-1}$
NMR (CDCl$_3$δ): 1.28–1.43 (24H, m), 4.26 (1H, t, J=20 Hz), 4.76–4.95 (4H, m), 7.17–7.36 (2H, m), 7.76 (1H, dd, J=8 and 2 Hz), 8.45 (1H, dd, J=8 and 2 Hz), 10.20 (1H, s)

Preparation 12

Tetraisopropyl [N-(4-fluorophenyl)thiocarbamoylmethylene]bis(phosphonate)
IR (Neat): 3480, 3300, 1510, 1000 cm$^{-1}$
NMR (CDCl$_3$, δ): 1.26–1.53 (24H, m), 4.32 (1H, t, J=24 Hz), 4.70–4.94 (4H, m), 7.04–7.13 (2H, m), 7.71–7.78 (2H, m), 10.19 (1H, s)

Preparation 13

Tetraisopropyl [N-(p-tolyl)thiocarbamoylmethylene]bis(phosphonate)
IR (Neat): 3500, 3300, 1535, 1385, 1260, 1000 cm$^{-1}$
NMR (CDCl$_3$, δ): 1.21–1.43 (24H, m), 2.35 (3H, s), 4.31 (1H, t, J=20 Hz), 4.70–4.94 (4H, m), 7.20 (2H, d, J=8 Hz), 7.65 (2H, d, J=8 Hz), 10.16 (1H, s)

Preparation 14

Tetraisopropyl [N-(2-methoxyphenyl)thiocarbamoyl-methylene]bis(phosphonate)
NMR (CDCl$_3$, δ): 1.18–1.50(24H, m), 3.92 (3H, m), 4.37 (1H, t, J=24 Hz), 4.73–4.93 (4H, m), 6.94–7.03 (2H, m), 7.16 (1H, td, J=8 and 2 Hz), 8.96 (1H, d, J=8 Hz), 10.45 (1H, s)

Preparation 15

Tetraisopropyl [N-(3,4-dichlorophenyl)thiocarbamoyl-methylene]bis(phosphonate)
mp: 90°–92° C.
IR (Nujol): 3300, 3200, 1260, 990 cm$^{-1}$
NMR (CDCl$_3$, δ): 1.32–1.71 (24H, m), 4.29 (1H, t, J=23 Hz), 4.67–4.94 (4H, m), 7.45 (1H, d, J=9 Hz), 7.65 (1H, dd, J=9 and 2 Hz), 8.14 (1H, d, J=2 Hz), 10.30 (1H, s)

Preparation 16

Tetraisopropyl [N-(2-benzo[b]thienyl)thiocarbamoyl-methylene]bis(phosphonate)

IR (Neat): 3500, 3210, 1600, 1580, 1380, 1260, 1100, 1000 cm$^{-1}$

NMR (CDCl$_3$, δ): 1.23-1.44 (24H, m), 4.31 (1H, t, J=22 Hz), 4.66-4.94 (4H, m), 7.26-7.40 (3H, m), 7.66-7.80 (2H, m), 11.11 (1H, s)

Preparation 17

Tetraisopropyl [N-(2-trifluoromethylphenyl)-thiocarbamoylmethylene]bis(phosphonate)

IR (Neat): 3330, 2980, 1530, 1460, 1380, 1320, 1260, 1170, 1140, 1100 cm$^{-1}$

NMR (CDCl$_3$, δ): 1.20-1.50 (24H, m), 4.48 (1H, t, J=23 Hz), 4.70-5.00 (4H, m), 7.41 (1H, t, J=8 Hz), 7.60 (1H, t, J=8 Hz), 7.72 (1H, d, J=8 Hz), 7.87 (1H, d, J=8 Hz), 9.91 (1H, s)

Preparation 18

Tetraisopropyl [N-(4-chloro-3-trifluoromethylphenyl)-thiocarbamoyl-methylene]bis(phosphonate)

mp: 101°-102°0 C.

IR (Nujol):3150, 3100, 1390, 1320, 1210, 1000 cm$^{-1}$
NMR (CDCl$_3$, δ): 1.25-1.46 (24H, m), 4.33 (1H, t, J=22 Hz), 4.74-4.97 (4H, m), 7.54 (1H, d, J=8 Hz), 8.05 (1H, dd, J=8 and 3 Hz), 8.22 (1H, d, J=3 Hz), 10.41 (1H, s)

Preparation 19

Tetraisopropyl [N-(4-methoxy-3-trifluoromethyl-phenyl)thiocarbamoylmethylene]bis(phosphonate)

IR (Neat): 3450, 3250, 1500, 1260, 1140 cm$^{-1}$ NMR (CDCl$_3$, δ): 1.34-1.44 (24H, m), 3.92 (3H, s), 4.32 (1H, t, J=23 Hz), 4.70-4.94 (4H, m), 7.02 (1H, d, J=8 Hz), 7.93 (1H, br s), 7.95 (1H, dd, J=8 and 2 Hz)

Preparation 20

Tetraisopropyl [N-(4-trifluoromethylphenyl)-carbamoylmethylene]bis(phosphonate)

mp: 136°-137° C.

IR (Nujol): 3250, 3200, 1670, 1600, 1540, 1320, 1250, 1120, 950 cm$^{-1}$

NMR (CDCl$_3$, δ): 1.30-1.42 (24H, m), 3.58 (1H, t, J=22 Hz), 4.73-4.91 (4H, m), 7.57 and 7.66 (each 2H, d, J=7 Hz), 9.05 (1H, s)

Preparation 21

Tetraisopropyl (N-methylcarbamoylmethylene)bis(phosphonate)

mp: 96°-100° C.

IR (Nujol): 3270, 1640, 1255, 980 cm$^{-1}$
NMR (CDCl$_3$, δ): 1.2-1.5 (24H, m), 2.85 (3H, d, J=4 Hz), 3.48 (1H, t, J=23 Hz), 4.65-4.95 (4H, m), 6.86 (1H, br)

Preparation 22

Tetraisopropyl [N-(n-butyl)thiocarbamoylmethylene]-bis(phosphonate)

IR (neat) : 3500, 3350, 1545, 1385, 1260 cm$^{-1}$

NMR (D$_2$O, δ): 0.95 (3H, t, J=7 Hz), 1.21-1.54 (26H, m), 1.59-1.74 (2H, m), 3.64 (2H, dt, J=7 Hz), 4.23 (1H, t, J=23 Hz), 4.65-4.89 (4H, m), 8.56 (1H, br m)

Preparation 23

Tetraisopropyl [N-(4-methylthiophenyl)thiocarbamoylmethylene]bis(phosphonate)

IR (Nujol) 1480, 1450, 1090, 920, 810 cm$^{-1}$

NMR (CDCl$_3$, δ): 1.15-1.5 (24H, m), 2.47 (1H, s), 4.27 (1H, t, J=21 Hz), 4.5-4.95 (4H, m), 7.26 (2H, d, J=8.6 Hz), 7.76 (2H, d, J=8.6 Hz), 10.2 (1H, s)

Preparation 24

Tetraisopropyl [N-(4-mesylaminophenyl)thiocarbamoylethylene]bis(phosphonate)

mp: 141°-143° C.

IR (Nujol): 3300, 3100, 1610, 1510, 1420, 1380, 1335, 1250, 1150, 1000 cm$^{-1}$ NMR (CDCl$_3$, δ): 1.33-1.67 (24H, m), 3.02 (3H, s), 4.30 (1H, t, J=23 Hz), 4.70-4.92 (4H, m), 7.29 and 7.50 (each 2H, d, J=9 Hz), 7.45 (1H, s), 10.23 (1H, s)

Preparation 25

Tetraisopropyl [N-(3-mesylaminophenyl)thiocarbamoylmethylene]-bis(phosphonate)

mp: 144°-145° C.

IR (Neat): 3450, 3150, 1600, 1380, 1240, 1150 cm$^{-1}$
NMR (CDCl$_3$, δ): 1.34-1.48 (24H, m), 3.06 (3H, s), 4.31 (1H, t, J=22 Hz), 4.73-4.91 (4H, m), 6.84 (1H, br s), 7.12 (1H, br d, J=6 Hz), 7.32-7.39 (2H, m), 7.98 (1H, br s), 10.29 (1H, br s)

Preparation 26

Tetraisopropyl [N-(4-acetylaminophenyl)thiocarbamoyl-methylene]-bis(phosphonate)

IR (Neat): 3500, 3300, 1690, 1515, 1385, 1260, 1100 cm$^{-1}$

NMR (CDCl$_3$, δ): 1.13-1.65 (24H, m), 2.21 (3H, s), 4.34 (1H, t, J=22 Hz), 4.58-4.98 (4H, m), 7.55 and 7.76 (2H, d, J=7 Hz), 10.20 (1H, s)

Preparation 27

Tetraisopropyl [N-(3-acetylaminophenyl)thiocarbamoyl-methylene]-bis(phosphonate)

IR (Neat): 3450, 3300, 1690, 1610, 1550, 1260, 1110 cm$^{-1}$

NMR (CDCl$_3$, δ): 1.10-1.62 (24H, m), 2.17 (3H, s), 4.30 (1H, t, J=22 Hz), 4.55-5.00 (4H, m), 7.30-7.62 (3H, m), 8.15 (1H, s)

Preparation 28

A mixture of tetraisopropyl methylenebis(phosphonate) (668 mg) and potassium tert-butoxide (224 mg) in anhydrous toluene, (5 ml) was refluxed for 1 hour. After cooling to ambient temperature, 3-(2-pyridyl)-3,4-dihydro-2H-pyrido[1,2-a]-1,3,5-triazin-2,4-dione (2.0 g) and anhydrous tetrahydrofuran (25 ml) were added to the solution, and the mixture was stirred at 60° C. for 30 minutes. The reaction mixture was cooled in an ice-water bath and then quenched with 1N hydrochloric acid. The organic layer was separated and the aqueous layer was extracted with ethyl acetate. The combined organic layer was washed with brine, dried, and evaporated in vacuo. The residue was subjected to column chromatography on silica gel eluted with methanol-methylene chloride-diethyl ether (1:10:30 V/V) to give tetraisopropyl [N-(2-pyridyl)carbamoylmethylene]bis(phosphonate)(1.42 g) as an oil.

IR (Neat): 3360, 3250, 1690 cm$^{-1}$

NMR (CDCl$_3$, δ): 1.20–1.58 (24H, m), 2.30 (1H, br s), 3.60 (1H, t, J=20 Hz), 4.67–5.05 (4H, m), 7.06 (1H, dd, J=7 and 5 Hz), 7.60–7.77 (1H, m), 8.12 (1H, d, J=7 Hz), 8.30 (1H, br d, J=5 Hz), 9.11 (1H, br s)

Preparation 29

To a solution of 2-benzo[b]thiophenecarbonyl chloride prepared from 2-benzo[b]thiophenecarboxylic acid (356 mg) and oxalyl chloride (0.35 ml) in methylene chloride (2 ml) was added dropwise a mixture of tetraethyl (aminomethylene)bis(phosphonate) (606 mg), pyridine (316 mg) and trace amounts of 4-(dimethylamino)-pyridine in methylene at 5° C. The mixture was stirred for 2 chloride (8 ml) hours at ambient temperature followed by the addition of ethyl acetate. The mixture was washed with water, 1N hydrochloric acid, saturated aqueous solution of sodium bicarbonate and brine successively. The organic layer was dried over magnesium sulfate and concentrated under reduced pressure. The residue was treated with diisopropyl ether to give tetraethyl [(2-benzo[b]thiophenecarboxamido)-methylene]-bis(phosphonate) (790 mg) as a white powder which was recrystallized from a mixture of ethyl acetate and n-hexane.

mp: 120°–121° C.

IR (Nujol): 3210, 1640, 1630 cm$^{-1}$

NMR (CDCl$_3$, δ): 1.30–1.42 (12H, m), 4.09–4.41 (8H, m), 5.22 (1H, td, J=20 and 9 Hz), 6.63 (1H, d, J=9 Hz), 7.38–7.50 (2H, m), 7.85 (1H, s), 7.85–7.92 (2H, m)

The following compounds (Preparations 30 to 33) were obtained according to a similar manner to that of Preparation 29.

Preparation 30

Tetraethyl [(2-quinolinecarboxamido)methylene]-bis(phosphonate)

mp: 58°–59° C. IR (Nujol) : 3500, 3400, 1680 cm$^{-1}$

NMR (CDCl$_3$, δ): 1.10–1.55 (12H, m), 1.04–4.45 (8H, m), 5.24 (1H, td, J=20 and 9 Hz), 7.65 (1H, t, J=7 Hz), 7.32 (1H, t, J=7 Hz), 7.90 (1H, d, J=7 Hz), 8.17 (1H, d, J=7 Hz), 8.29 (2H, q, J=10 and 8 Hz), 8.25 (1H, d, J=9 Hz)

Preparation 31

Tetraethyl (benzoylaminomethylene)bis(phosphonate)

IR (CHCl$_3$, δ) 3430, 1665, 1600, 1580, 1480, 1390, 1368 cm$^{-1}$

NMR (CDCl$_3$δ): 1.31 (6H, t, J=7 Hz), 1.35 6H, t, J=7 Hz), 4.05–4.35 (8H, m), 5.26 (1H, dt, J=10, 22 Hz), 6.77 (1H, d, J=10 Hz), 7.40–7.60 (3H, m), 7.81 (2H, d, J=8 Hz)

Preparation 32

Tetraethyl [(4-chlorobenzoylamino)methylene]bis-(phosphonate)

NMR (CDCl$_3$, δ): 1.31 (6H, t, J=7 Hz), 1.35 (6H, t, J=7 Hz), 4.22 (4H, q, J=7 Hz), 4.23 (4H, q, J=7 Hz), 5.24 (1H, dt, J=10, 22 Hz), 4.23 (4H, q, J=7 Hz), 5.24 (1H, dt, J=10, 22 Hz), 6.82 (1H, d, J=10 Hz), 7.44 (2H, d, J=8 Hz), 7.74 (2H, d, J=8 Hz)

Preparation 33

Tetraethyl [(2-pyridinecarboxamido)methylene]-bis(phosphonate)

IR (Neat) : 3500, 3400 1685 cm$^{-1}$

NMR (CDCl$_3$, δ): 1.28–1.37 (12H, m), 4.15–4.32 (8H, m), 5.18 (1H, td, J=20 and 10 Hz), 7.27–7.51 (1H, m), 7.82–7.91 (1H, td, J=8 and 2 Hz), 8.17 (1H, d, J=8 Hz), 8.54 (1H, d, J=10 Hz), 8.58–8.62 (1H, m)

Preparation 34

To a solution of 2-[1-(tert-butoxycarbonyl)-imidazol-4-yl]acetic acid (45 mg) and tetraethyl (aminomethylene)bis(phosphonate) (91 mg) in N,N-dimethylformamide (1 ml) was added N-ethyl-N'-(3-dimethylaminopropyl)carbodiimide hydrochloride (42 mg) with stirring on ice-sodium chloride bath under nitrogen atmosphere. After stirring for 36 hours at 5° C., the mixture was diluted with chloroform (10 ml) and washed with cold 1N aqueous solution of citric acid (10 ml). The aqueous layer was extracted with chloroform (10 ml) twice and the combined organic layers were dried over sodium sulfate and evaporated in vacuo. The residue was dissolved in ethyl acetate (10 ml) and the solution was washed with water (10 ml), dried over sodium sulfate and evaporated in vacuo to give a colorless syrup of tetraethyl [[2-{1-(tert-butoxycarbonyl)-imidazol-4-yl}acetamido]methylene]bis(phosphonate) (67 mg).

NMR (CDCl$_3$, δ): 1.32 (6H, t, J=6 Hz), 1.33 (6H, t, J=6 Hz), 1.62 (9H, s), 3.60 (2H, s), 4.1–4.3 (8H, m), 5.06 (1H, dt, J=12 Hz, 24 Hz), 7.28 (1H, s), 7.59 (1H, d, J=12 Hz), 8.07 (1H, s)

Preparation 35

To a solution of tetraethyl (aminomethylene)bis-(phosphonate) (661 mg) in pyridine (2 ml) were added benzenesulfonyl chloride (0.35 ml) and then 4-(dimethylamino)pyridine (50 mg) at ambient temperature with stirring. After stirring for 4 hours at the same temperature, the reaction mixture was diluted with ethyl acetate (20 ml). The mixture was washed with 1N hydrochloric acid four times, water and saturated aqueous hydrogen bicarbonate solution successively. The organic layer was dried over magnesium sulfate and evaporated under reduced pressure. The residue was subjected to column chromatography on silica gel (20 g) eluted with a mixture of chloroform and methanol (20:1 V/V) to give tetraethyl (phenylsulfonylaminomethylene)bis(phosphonate) as a yellow syrup (364 mg).

IR (CHCl$_3$, δ): 3390, 3000, 1343, 1256, 1165 cm$^{-1}$

NMR (CDCl$_3$, δ): 1.25 (6H, t, J=7 Hz), 1.28 (6H, t, J=7 Hz), 3.90–4.20 (8H, m), 4.23 (1H, t, J=22 Hz), 5.68 (1H, br s), 7.45–7.60 (3H, m), 7.91 (2H, dd, J=2, 8 Hz)

The following compounds (Preparations 36 to 40) were obtained according to a similar manner to that of Preparation 35.

Preparation 36

Tetraethyl (tosylaminomethylene)bis(phosphonate)

NMR (CDCl$_3$, δ): 1.2–1.45 (12H, m), 2.42 (3H, s), 3.9–4.4 (9H, m), 7.3 and 7.75 (4H, ABq, J=8.4 Hz)

Preparation 37

Tetraethyl [(4-chlorophenyl)sulfonylaminomethylene]-bis(phosphonate)

mp: 130°–131° C.

NMR (CDCl$_3$, δ): 1.27 (6H, t, J=6 Hz), 1.30 (6H, t, J=6 Hz), 3.90–4.30 (8H, m), 5.32 (1H, br s), 7.48 (2H, d, J=8 Hz), 7.84 (2H, d, J=8 Hz)

Preparation 38

Tetraethyl [(3,4-dichlorophenyl)sulfonylaminomethylene]-bis(phosphonate)

mp: 104°–106° C.

IR (Nujol): 3600, 3400, 3000, 1630, 1200, 1160, 1070 cm$^{-1}$

NMR (CDCl$_3$, δ): 1.20–1.40 (12H, m), 4.00–4.40 (9H, m), 7.58 (1H, d, J=8.5 Hz), 7.74 (1H, dd, J=9.0 and 2 Hz), 7.99 (1H, d, J=2 Hz)

Preparation 39

Tetraethyl [(2-thienyl)sulfonylaminomethylene]bis-(phosphonate)

IR (Neat): 3070, 2960, 1255, 1155, 1020 cm$^{-1}$

NMR (CDCl$_3$, δ): 1.2–1.5 (12H, m), 2.3 (1H, br), 4.0–4.35 (9H, m), 7.09 (1H, dd, J=4 Hz and 5 Hz), 7.60 (1H, dd, J=Hz and 5 Hz), 7.66 (1H, dd, J=1Hz and 4 Hz)

Preparation 40

Tetraethyl [(8-quinolyl)sulfonylaminomethylene]-bis(phosphonate)

NMR (CDCl$_3$, δ): 1.10 (6H, t, J=7 Hz), 1.19 (6H, t, J=7 Hz), 3.80–4.20 (8H, m), 4.40 (1H, t, J=22 Hz), 7.57 (1H, dd, J=8,4 Hz), 7.65 (1H, t, J=8 Hz), 8.06 (1H, d, J=8 Hz), 8.29 (1H, dd, J=8, 2 Hz), 8.33 (1H, d, J=8 Hz), 9.07 (1H, dd, J=4, 2 Hz)

Preparation 41

To a suspension of sodium hydride (44 mg, 63.9% oil dispersion) in distilled tetrahydrofuran (2.0 ml) was added tetraisopropyl methylenebis(phosphonate) (344 mg) in one portion at 5° C. The mixture was stirred for 30 minutes at ambient temperature and then cooled in an ice bath, followed by addition of 4-chlorophenyl isocyanate (154 mg). The mixture was stirred for 30 minutes at 5° C. and for one hour at ambient temperature to give a solution including sodium salt of tetraisopropyl [N-(4-chlorophenyl)carbamoylmethylene]-bis(phosphonate). Methyl iodide (426 mg) was added thereto at ambient temperature. The solution was stirred for 5 hours at the same temperature and quenched with aqueous solution of ammonium chloride. The separated oil was extracted with ethyl acetate. The extract was washed with brine, dried, and evaporated under reduced pressure. The residue was subjected to column chromatography on silica gel using a mixture of n-hexane and ethyl acetate (1:1 V/V) as an eluent to give tetraisopropyl 1-[N-(4-chlorophenyl)-carbamoyl]ethane-1,1-bis(phosphonate) (399 mg) as a colorless oil.

IR (Nujol): 3350, 1695 cm$^{-1}$

NMR (CDCl$_3$, δ): 1.20–1.55 (24H, m), 1.70 (3H, t, J=14 Hz), 4.68–4.92 (4H, m), 7.28 (2H, d, J=8 Hz), 7.52 (2H, d, J=8 Hz), 9.29 (1H, s)

The following compounds (Examples 1 to 31) were obtained according to a similar manner to that of Preparation 2.

Example 1

Tris(tert-butylamine) salt of [N-(phenyl)thiocarbamoylmethylene]bis(phosphonic acid)

mp: 140° C.

NMR (D$_2$O, δ): 1.35 (27H, br s), 4.05 (1H, t, J=20 Hz), 7.3–7.75 (5H, m)

Example 2

Tris(tert-butylamine) salt of [N-(4-chlorophenyl)carbamoylmethylene]bis(phosphonic acid)

mp: 206°–210° C.

IR (Nujol): 3700–2000, 1660, 1540, 1150, 1090, 825 cm$^{-1}$

NMR (D$_2$O, δ): 1.4 (27H, br s), 3.23 (1H, t, J=20 Hz), 7.40 and 7.50 (4H, ABq, J=9 Hz)

Example 3

Tris(tert-butylamine) salt of [N-(phenyl)carbamoylmethylene]bis(phosphonic acid)

mp: 207°–209° C.

IR (Nujol): 3700–2000, 1650, 1600, 1150, 1130, 1065, 960 cm$^{-1}$

NMR (D$_2$O, δ): 1.40 (27H, br s), 3.25 (1H, t, J=20 Hz), 7.15–7.6 (5H, m)

Example 4

Tris(tert-butylamine) salt of [N-(4-fluorophenyl)-carbamoylmethylene]bis(phosphonic acid)

mp: 209°–211° C.

IR (Nujol): 3700–2000 (br), 1650 cm$^{-1}$ 7.14 (2H, t, J=8 Hz), 7.50 (2H, dd, J=8 and 5 Hz)

Example 5

Tris(tert-butylamine) salt of [N-(3,4-dichlorophenyl)carbamoylmethylene]bis(phosphonic acid)

mp: 216°–220° C.

IR (Nujol ): 3600–2100 (br), 1660 cm$^{-1}$

NMR (D$_2$, δ): 1.35 (27H, s), 3.30 (1H, t, J=20 Hz), 7.38 (1H, dd, J=9 and 2 Hz), 7.50 (1H, d, J=9 Hz), 7.81 (1H, d, J=2 Hz)

Example 6

Tris(tert-butylamine) salt of [N-(p-tolyl)carbamoylmethylene]bis(phosphonic acid)

mp: 221°–230° C.

IR (Nujol): 3700–2000 (br), 1655 cm$^{-1}$

NMR (D$_2$O, δ): 1.36 (27H, s), 2.32 (3H, s), 3.27 (1H, t, J=20 Hz), 7.25 (2H, d, J=8 Hz), 7.40 (2H, d, J=8 Hz)

Example 7

Tris(tert-butylamine) salt of [N-(4-methoxyphenyl)-carbamoylmethylene]bis(phosphonic acid)

mp: 214°–220° C.
IR (Nujol): 3700–2300 (br), 1650 cm$^{-1}$
NMR (D$_2$O, δ): 1.37 (27H, s), 3.27 (1H, t, J=20 Hz), 3.85 (3H, s), 7.02 (2H, d, J=8 Hz), 7.45 (2H, d, J=8 Hz)

Example 8

Tris(tert-butylamine) salt of 1-[N-(4-chlorophenyl)carbamoyl]ethane-1,1-bis(phosphonic acid)

mp: 237°–239° C.
IR (Nujol): 3700–2000 (br), 1650 cm$^{-1}$
NMR (D20, 6): 1.36 (27H, s), 1.56 (3H, t, J=14 Hz), 7.38 (2H, d, J=8 Hz), 7.50 (2H, d, J=8 Hz)

Example 9

Tris(tert-butylamine) salt of [N-(4-chlorophenyl)thiocarbamoylmethylene]bis(phosphonic acid)

mp: 206°–208° C.
NMR (D$_2$O, 6): 1.34 (27H, m), 4.08 (1H, t, J=22 Hz), 7.47 and 7.60 (4H, ABq, J=8 Hz)

Example 10

Bis(tert-butylamine) salt of [N-(1-naphthyl)thiocarbamoylmethylene]bis(phosphonic acid)

mp: 160° C. (dec.)
NMR (D$_2$O, δ): 1.35 (18H, s), 4.24 (1H, t, J=22 Hz), 7.60–8.23 (7H, m)

Example 11

Disodium salt of [N-(3-trifluoromethylphenyl)thiocarbamoylmethylene]bis(phosphonic acid)

mp: 218° C. (dec.)
IR (Nujol): 3300, 1600, 1410, 1170, 1130, 1070, 890 cm$^{-1}$
NMR (D$_2$O, δ): 4.21 (1H, t, J=20 Hz), 7.60–7.77 (2H, m), 7.82 (1H, m), 8.10 (1H, s)

Example 12

Disodium salt of [N-(4-trifluoromethylphenyl)thiocarbamoylmethylene]bis(phosphonic acid)

mp: 218° C. (dec.)
IR (Nujol) : 3260, 1610, 1425, 1400, 1335, 1170, 1065 cm$^{-1}$
NMR (D$_2$O, δ): 4.11 (1H, t, J=20.7 Hz), 7.80 and 7.88 (4H, ABq, J=8.8 Hz)

Example 13

Disodium salt of [N-(3-chlorophenyl)thiocarbamoyl-methylene]bis(phosphonic acid)

mp: 224° C. (dec.)
IR (Nujol) : 3300, 3200, 2350, 1595, 1400, 1255, 1200, 1170, 1090 cm$^{-1}$
NMR (D$_2$O, δ): 4.12 (1H, t, J=20 Hz), 7.31–7.56 (3H, m), 7.88 (1H, s)

Example 14

Disodium salt of [N-(2-chlorophenyl)thiocarbamoyl-methylene]bis(phosphonic acid)

mp: 255°–257° C. (dec.)
IR (Nujol): 3700–2400 (br), 1590, 1150, 1120 cm$^{-1}$

Example 15

Disodium salt of [N-(4-fluorophenyl)thiocarbamoyl-methylene]bis(phosphonic acid)

mp: 247°–249° C. (dec.)
IR (Nujol): 3700–2300 (br), 1220, 1090 cm$^{-1}$
NMR (D$_2$O, δ): 4.10 (1H, t, J=21 Hz), 7.21 (2H, t, J=9 Hz), 7.58 (2H, dd, J=9 and 5 Hz)

Example 16

Disodium salt of [N-(p-tolyl)thiocarbamoylmethylene]-bis(phosphonic acid)

mp: 255°–258° C. (dec.)
IR (Nujol) : 3700–2300 (br.), 1520, 1150 cm$^{-1}$
NMR (D$_2$O, δ): 2.37 (3H, s), 4.04 (1H, t, J=20 Hz), 7.32 and 7.52 (2H, dd, J=8 Hz)

Example 17

Disodium salt of [N-(2-methoxyphenyl)thiocarbamoylmethylene]bis(phosphonic acid)

mp: 227° C. (dec.)
IR (Nujol) : 3605, 3350, 1600, 1540, 1400, 1240, 1160, 1050 cm$^{-1}$
NMR (D$_2$O, δ) : 3.90 (3H, s), 4.09 (1H, t, J=20 Hz), 7.03–7.19 (2H, m), 7.37 (1H, t, J=8 Hz), 8.14 (1H, d, J=8 Hz)

Example 18

Disodium salt of [N-(3,4-dichlorophenyl)thiocarbamoylmethylene]bis(phosphonic acid)

mp: 248°–250° C. (dec.)
IR (Nujol): 3700–2300 (br), 1190, 1090 cm$^{-1}$
7.53–7.64 (2H, m), 8.03 (1H, s)

Example 19

Disodium salt of [N-(2-pyridyl)carbamoylmethylene]-bis(phosphonic acid)

mp: >300° C.
IR (Nujol): 3700–2100 (br), 1675 cm$^{-1}$
NMR (D$_2$O, δ): 3.47 (1H, t, J=20 Hz), 7.27 (1H, t, J=6 Hz), 7.83 (1H, d, J=8 Hz), 7.95 (1H, t, J=8 Hz), 8.29 (1H, d, J=6 Hz)

Disodium salt of [N-(2-benzo[b]thienyl)-thiocarbamoylmethylene]bis(phosphonic acid)

mp: >280° C.
IR (Nujol): 3700–2300 (br), 1460, 1410, 1230, 1160 cm$^{-1}$
NMR (D$_2$O, δ): 4.02 (1H, t, J=20 Hz), 7.35–7.47 (2H, m), 7.45 (1H, s), 7.85 (1H, d, J=11 Hz), 7.97 (1H, d, J=15 Hz)

Example 21

Disodium salt of
[N-(2-trifluoromethylphenyl)thiocarbamoylmethylene]bis(phosphonic acid)

mp: 212° C. (dec.)

IR (Nujol) : 3250, 2400, 1530, 1410, 1320, 1150, 1060 cm$^{-1}$

NMR (D$_2$O, δ) : 4.16 (1H, t, J=21 Hz), 7.52–7.60 (1H, m), 7.65–7.76 (2H, m), 7.83 (1H, d, J=8 Hz)

Example 22

Disodium salt of
[N-(4-chloro-3-trifluoromethylphenyl)thiocarbamoylmethylene]bis(phosphonic acid)

mp: 245° C. (dec.)

IR (Nujol):3350, 3200, 1620, 1560, 1485, 1415, 1320 cm$^{-1}$

NMR (D$_2$O, δ): 4.00 (1H, t, J=20 Hz), 7.68 (1H, d, J=9 Hz), 7.88 (1H, d, J=9 Hz), 8.29 (1H, s)

Example 23

Disodium salt of
[N-(4-methoxy-3-trifluoromethylphenyl)thiocarbamoylmethylene]bis(phosphonic acid)

mp: 249°–252° C. (dec.)

IR (Nujol) : 3250, 2350, 1505, 1325, 1280, 1130 cm$^{-1}$

NMR (D$_2$O, δ): 4.05 (1H, t, J=20 Hz), 7.28 (1H, d, J=9 Hz), 7.77 (1H, d, J=9 Hz), 7.97 (1H, d, J=2 Hz)

Example 24

Bis(tert-butylamine) salt of
(N-methylcarbamoylmethylene)bis(phosphonic acid)

mp: 229° C. (dec.)

IR (Nujol) : 3600–2000, 1645, 1150 cm$^{-1}$

NMR (D$_2$O, δ): 1.36 (18H, s), 2.79 (3H, s), 3.22 (1H, t, J=21 Hz)

Example 25

Disodium salt of
[N-(n-butyl)thiocarbamoylmethylene]-bis(phosphonic acid)

mp: >250° C.

IR (Nujol) : 3500, 3250, 1560, 1280, 1180, 1065 cm$^{-1}$

NMR (D$_2$O, δ): 0.94 (3H, t, J=7 Hz), 1.33–1.51 (2H, m), 1.51–1.69 (2H, m), 3.61 (2H, t, J=8 Hz), 3.91 (1H, t, J=21 Hz)

Example 26

Disodium salt of
[N-(4-trifluoromethylphenyl)carbamoylmethylene]bis(-phosphonic acid)

mp:>250° C.

IR (Nujol) : 3700–3000 (br), 2300, 1650, 1600, 1335, 1100 cm

NMR (D$_2$O, δ): 3.31 (1H, t, J=20 Hz), 7.70 (4H, s)

Example 27

Disodium salt of
[N-(4-methylthiophenyl)thiocarbamoylmethylene]bis(-phosphonic acid)

mp: 215° C. (dec.)

IR (Nujol) : 3500, 3300, 1500, 1390, 1170, 1065 cm$^{-1}$

NMR (D$_2$O, δ): 2.5 (1H, s), 4.09 (1H, t, J=21 Hz), 7.4 (2H, d, J=8.6 Hz), 7.59 (2H, d, J=8.6 Hz)

Example 28

Disodium salt of
[N-(4-mesylaminophenyl)-thiocarbamoylmethylene]-bis(phosphonic acid)

mp: 225° C. (dec.)

IR (Nujol) : 3200, 2350, 1510, 1320, 1150 cm$^{-1}$

NMR (D$_2$O, δ): 3.12 (3H, s), 4.08 (1H, t, J=20 Hz), 7.34 and 7.65 (each 2H, d, J=9 Hz)

Example 29

Disodium salt of
[N-(3-mesylaminophenyl)-thiocarbamoylmethylene]-bis(phosphonic acid)

mp: 212° C. (dec.)

IR (Nujol) : 3300, 2400, 1620, 1340, 1160, 1080 cm$^{-1}$

NMR (D$_2$O, δ): 3.12 (3H, s), 4.80 (1H, t, J=20 Hz), 7.22–7.25 (1H, br d, J=6 Hz), 7.45–7.49 (2H, m), 7.73 (1H, br s)

Example 30

Disodium salt of
[N-(4-acetylaminophenyl)thiocarbamoylmethylene]-bis(phosphonic acid)

mp: 218° C. (dec.)

IR (Nujol): 3250, 2350, 1660, 1510, 1400, 1140, 1060 cm$^{-1}$

NMR (D$_2$O, δ): 2.18 (3H, s), 4.80 (1H, t, J=20 Hz), 7.50 and 7.64 (2H, d, J=8 Hz)

Example 31

Disodium salt of
[N-(3-acetylaminophenyl)-thiocarbamoyl]methylenebis(phosphonic acid)

mp: 209° C. (dec.)

IR (Nujol) : 3200, 2350, 1670, 1605, 1550, 1160, 1080 cm$^{-1}$

NMR (D$_2$O, δ): 2.16 (3H, s), 4.80 (1H, t, J=20 Hz), 7.35–7.57 (2H, m), 7.76 (1H, br s)

The following compounds (Examples 32 and 37) were obtained according to a similar manner to that of Preparation 29.

EXAMPLE 32

Bis(tert-butylamine) salt of
[(2-benzo[b]thiophenecarboxamido)methylene]bis(-phosphonic acid)

mp: 234°–238° C.

IR (Nujol): 3700–2050 (br), 1640 cm$^{-1}$

NMR (D$_2$O, δ): 1.40 (18H, s), 4.59 (1H, t, J=20 Hz), 7.43–7.58 (2H, m), 7.95–8.08 (2H, m), 8.11 (1H, s)

EXAMPLE 33

Tris(tert-butylamine)salt of
[(2-quinolinecarboxamido)methylene]bis(phosohonic acid)

IR (Nujol): 3700–2000 (br), 1660 cm$^{-1}$

NMR (D$_2$O, δ): 1.46 (27H, s), 4.61 (1H, t, J=20 Hz), 7.76 (1H, t, J=11 Hz), 7.94 (1H, t, J=11 Hz), 8.08 (1H, d, J=8 Hz), 8.20 (2H, t, J=11 Hz), 8.58 (1H, d, J=8 Hz)

EXAMPLE 34

Disodium salt of
(benzoylaminomethylene)bis-(phosphonic acid)

mp: >260° C.

NMR (D$_2$O, δ): 4.66 (1H, t, J=20 Hz), 7.20–7.50 (3H, m), 7.85 (2H, d, J=8 Hz)

EXAMPLE 35

Disodium salt of [(4-chlorobenzoylamino)methylene]-bis(phosphonic acid)

mp: >260° C.

NMR (D$_2$O, δ): 4.65 (1H, t, J=20 Hz), 7.55 (2H, d, J=9 Hz), 7.83 (2H, d, J=9 Hz)

EXAMPLE 36

Disodium salt of [(2-pyridinecarboxamido)methylene]bis(phosphonic acid)

mp: >300° C.

IR (Nujol): 3700–2300 (br), 1670 cm$^{-1}$

NMR (D$_2$O, δ): 4.64 (1H, t, J=20 Hz), 7.64–7.71 (1H, m), 8.04–8.14 (2H, m), 8.66 (1H, d, J=5 Hz)

EXAMPLE 37

[{2-(Imidazol-4-yl)acetamido}methylene]bis-(phosphonic acid)

mp: 247°–250° C.

NMR (D$_2$O, δ): 3.77 (2H, s), 4.55 (1H, t, J=21 Hz), 7.24 (1H, s), 8.51 (1H, s)

The following compounds (Examples 38 to 43) were obtained according to a similar manner to that of Preparation 35.

EXAMPLE 38

(Phenylsulfonylaminomethylene)bis(phosphonic acid)

mp: 215°–215° C.

NMR (D$_2$O, δ): 3.95 (1H, t, J=21 Hz), 7.50–7.70 (3H, m), 7.89 (1H, dd, J=1, 8 Hz)

EXAMPLE 39

(Tosylaminomethylene)bis(phosphonic acid)

mp: 232°–233° C.

NMR (D$_2$O, δ): 3.98 (1H, t, J=21 Hz), 7.78 and 7.41 (4H, ABq, J=8.1 Hz)

EXAMPLE 40

Disodium salt of [(4-chlorophenyl)sulfonylaminomethylene]bis(phosphonic acid)

mp: >260° C.

NMR (D$_2$O, δ): 3.80 (1H, t, J=20 Hz), 7.59 (2H, d, J=8 Hz), 7.88 (2H, d, J=8 Hz)

EXAMPLE 41

[(3,4-Dichlorophenyl)sulfonylaminomethylene]bis(phosphonic acid)

mp: >250° C.

IR (Nujol): 3100, 1345, 1270, 1230, 1050 cm$^{-1}$

NMR (D$_2$O, δ): 3.74 (1H, t, J=20 Hz), 7.70 (1H, d, J=9 Hz), 7.80 (1H, d, J=9 Hz), 8.09 (1H, s)

EXAMPLE 42

(2-Thienyl)sulfonylaminomethylene]bis(phosphonic acid)

mp: 231° C. (dec.)

IR (Nujol): 3540, 1325, 1165 cm$^{-1}$

NMR (D$_2$O, δ): 3.98 (1H, t, J=21 Hz), 7.1–7.2 (1H, m), 7.73 (1H, d, J=3.5 Hz), 7.79 (1H, d, J=5 Hz)

EXAMPLE 43

Disodium salt of [(8-quinolyl)sulfonylaminomethylene]bis(phosphonic acid)

mp: >260° C.

NMR (D$_2$O, δ): 3.65 (1H, t, J=19 Hz), 7.61 (1H, dd, J=3, 7 Hz), 7.65 (1H, t, J=7 Hz), 8.11 (1H, d, J=7 Hz), 8.40 (1H, d, J=7 Hz), 8.44 (1H, d, J=7 Hz), 8.96 (1H, d, J=3 Hz)

EXAMPLE 44

To a solution of tetraisopropyl [N-(phenyl)thiocarbamoylmethylene]bis(phosphonate) (3.101 g) in methylene chloride (4 ml) was added iodotrimethylsilane (0.18 ml) in one portion at 5° C. The mixture was stirred for 30 minutes at ambient temperature and then extracted with water. The aqueous layer was washed with methylene chloride and the solvent was removed azeotropically with toluene under reduced pressure. The residue containing [N-(phenyl)thiocarbamoylmethylene]bis(phosphonic acid) was dissolved in ethanol (2.1 ml) and tert-butylamine (0.11 ml) was added thereto. The solvent was removed and the residue was pulverized with a mixture of ethanol and diethyl ether. The powder was dissolved in water and lyophilized to give tris(tert-butylamine)salt of [N-(phenyl)thiocarbamoylmethylene]bis(phosphonic acid) (93 mg) as a colorless powder.

mp: 140° C.

NMR (D$_2$O, δ): 1.35 (27H, br s), 4.05 (1H, t, J=20 Hz), 7.3–7.75 (5H, m)

The following compounds (Examples 45 to 54) were obtained according to a similar manner to that of Example 44.

EXAMPLE 45

Tris(tert-butylamine) salt of [N-(4-chlorophenyl)-carbamoylmethylene]bis(phosphonic acid)

mp: 206°–210° C.

IR (Nujol): 3700–2000, 1660, 1540, 1150, 1090, 825 cm$^{-1}$

NMR (D$_2$O, δ): 1.4 (27H, br s), 3.23 (1H, t, J=20 Hz), 7.40 and 7.50 (4H, ABq, J=9 Hz)

EXAMPLE 46

Tris(tert-butylamine) salt of [N-(phenyl)carbamoylmethylene]bis(phosphonic acid)

mp: 207°–209° C.

IR (Nujol): 3700–2000, 1650, 1600, 1150, 1130, 1065, 960 cm$^{-1}$

NMR (D$_2$O, δ): 1.40 (27H, br s), 3.25 (1H, t, J=20 Hz), 7.15–7.6 (5H, m)

EXAMPLE 47

Tris(tert-butylamine) salt of [N-(4-fluorophenyl)-arbamoylmethylene]bis(phosphonic acid)

mp: 209°–211° C.

IR (Nujol): 3700–2000 (br), 1650 cm$^{-1}$

NMR (D$_2$O, δ): 1.36 (27H, s), 3.23 (1H, t, J=20 Hz), 7.14 (2H, t, J=8 Hz), 7.50 (2H, dd, J=8 and 5 Hz)

EXAMPLE 48

Tris(tert-butylamine) salt of [N-(3,4-dichlorophenyl)carbamoylmethylene]bis(phosphonic acid)

mp: 216°–220° C.
IR (Nujol): 3600–2100 (br), 1660 cm$^{-1}$
NMR (D$_2$O, δ): 1.35 (27H, s), 3.30 (1H, t, J=20 Hz), 7.38 (1H, dd, J=9 and 2 Hz), 7.50 (1H, d, J=9 Hz), 7.81 (1H, d, J=2 Hz)

EXAMPLE 49

Tris(tert-butylamine) salt of [N-(p-tolyl)carbamoylmethylene]bis(phosphonic acid)

mp: 221°–230° C.
IR (Nujol): 3700–2000 (br), 1655 cm$^{-1}$
NMR (D$_2$O, δ): 1.36 (27H, s), 2.32 (3H, s), 3.27 (1H, t, J=20 Hz), 7.25 (2H, d, J=8 Hz), 7.40 (2H, d, J=8 Hz)

EXAMPLE 50

Tris(tert-butylamine) salt of [N-(4-methoxyphenyl)carbamoylmethylene]bis(phosphonic acid)

mp 214°–220° C.
IR (Nujol): 3700–2300 (br), 1650 cm$^{-1}$
NMR (D$_2$O, δ): 1.37 (27H, s), 3.27 (1H, t, J=20 Hz), 3.85 (3H, s), 7.02 (2H, d, J=8 Hz), 7.45 (2H, d, J=8 Hz)

EXAMPLE 51

Tris(tert-butylamine) salt of 1-[N-(4-chlorophenyl)-carbamoyl]ethane-1,1-bis(phosphonic acid)

mp: 237°–239° C.
IR (Nujol): 3700–2000 (br)., 1650 cm$^{-1}$
NMR (D$_2$O, δ): 1.36 (27H, s), 1.56 (3H, t, J=14 Hz), 7.38 (2H, d, J=8 Hz), 7.50 (2H, d, J=8 Hz)

EXAMPLE 52

Tris(tert-butylamine) salt of [N-(4-chlorophenyl)thiocarbamoylmethylene]bis(phosphonic acid)

mp: 206°–208° C.
NMR (D$_2$O, δ): 1.34 (27H, m), 4.08 (1H, t, J=22 Hz), 7.47 and 7.60 (4H, ABq, J=8 Hz)

EXAMPLE 53

Bis(tert-butylamine) salt of [N-(1-naphthyl)thiocarbamoylmethylene]bis(phosphonic acid)

mp: 160° C. (dec.)
NMR (D$_2$O, δ): 1.35 (18H, s), 4.24 (1H, t, J=22 Hz), 7.60–8.23 (7H, m)

EXAMPLE 54

Bis(tert-butylamine) salt of (N-methylcarbamoylmethylene)bis(phosphonic acid)

mp: 229° C. (dec.)
IR (Nujol): 3600–2000, 1645, 1150 cm$^{-1}$
NMR (D$_2$O, δ): 1.36 (18H, s), 2.79 (3H, s), 3.22 (1H, t, J=21 Hz)

EXAMPLE 55

To a solution of tetraisopropyl [N-(3-trifluoromethylphenyl)thiocarbamoylmethylene]bis(phosphonate) (2 g) in methylene chloride (36 ml) was added iodotrimethylsilane (2.86 ml) at 0° C. and the mixture was stirred for 4 hours at the same temperature. Water (40 ml) was poured into the reaction mixture and the separated residue was aqueous layer was washed four times with methylene chloride and concentrated. The residue was dissolved in acetonitrile (30 ml) and tert-butylamine (534 mg) was added thereto. The resulting precipitate was collected by filtration and tert-butylamine (534 mg) was added to the filtrate. The resulting precipitate was collected by filtration. The obtained precipitates were combined and passed through the column chromatography on Dowex 50W×8 (H$^+$, 5 ml) (Trademark: manufactured by Dow Chemical Co.) with water. The elements were concentrated and the residue containing [N-(3-trifluoromethylphenyl)thiocarbamoylmethylene]bis(phosphonic acid) was dissolved in water (20 ml). To the solution was added sodium acetate (266 mg) and the mixture was stirred at 60° C. for 20 minutes and then heated at 100° C. with adding ethanol thereto. After the mixture was cooled, the, resulting precipitate was collected by filtration and dried in vacuo to give disodium salt of [N-(3-trifluoromathylphenyl)-thiocarbamoylmethylene]bis(phosphonic acid) (544 mg).

mp: 218° C. (dec.)
IR (Nujol): 3300, 1600, 1410, 1170, 1130, 1070, 890 cm$^{-1}$
NMR (D$_2$O, δ): 4.21 (1H, t, J=20 Hz), 7.60–7.77 (2H, m), 7.82 (1H, m), 8.10 (1H, s)

The following compounds (Examples 56 to 74) were obtained according to a similar manner to that of Example 55.

EXAMPLE 56

Disodium salt of [N-(4-trifluoromethylphenyl)thiocarbamoylmethylene]bis(phosphonic acid)

mp: 218° C. (dec.)
IR (Nujol): 3260, 1610, 1425, 1400, 1335, 1170, 1065 cm$^{-1}$
NMR (D$_2$O, δ): 4.11 (1H, t, J=20.7 Hz), 7.80 and 7.88 (4H, ABq, J=8.8 Hz)

EXAMPLE 57

Disodium salt of [N-(3-chlorophenyl)thiocarbamoylmethylene]bis(phosphonic acid)

mp: 224° C. (dec.)
IR (Nujol): 3300, 3200, 2350, 1595, 1400, 1255, 1200, 1170, 1090 cm$^{-1}$
NMR (D$_2$O, δ): 4.12 (1H, t, J=20 Hz), 7.31–7.56 (3H, m), 7.88 (1H, s)

EXAMPLE 58

Disodium salt of [N-(2-chlorophenyl)thiocarbamoylmethylene]bis(phosphonic acid)

mp: 255°–257° C. (dec.)
IR (Nujol): 3700–2400 (br), 1590, 1150, 1120 cm$^{-1}$

EXAMPLE 59

Disodium salt of [N-(4-fluorophenyl)thiocarbamoylmethylene]bis(phosphonic acid)

mp: 247°–249° C. (dec.)
IR (Nujol): 3700–2300 (br), 1220, 1090 cm$^{-1}$
NMR (D$_2$O, δ): 4.10 (1H, t, J=21 Hz), 7.21 (2H, t, J=9 Hz), 7.58 (2H, dd, J=9 and 5 Hz)

EXAMPLE 60

Disodium salt of
[N-(p-tolyl)thiocarbamoylmethylene]-bis(phosphonic acid)

mp: 255°–258° C. (dec.)
IR (Nujol): 3700–2300 (br), 1520, 1150 cm$^{-1}$
NMR (D$_2$O, δ): 2.37 (3H, s), 4.04 (1H, t, J=20 Hz), 7.32 and 7.52 (2H, dd, J=8 Hz)

EXAMPLE 61

Disodium salt of
[N-(2-methoxyphenyl)thiocarbamoylmethylene]bis(phosphonic acid)

mp: 227° C. (dec.)
IR (Nujol): 3605, 3350, 1600, 1540, 1400, 1240, 1160, 1050 cm$^{-1}$
NMR (D$_2$O, δ): 3.90 (3H, s), 4.09 (1H, t, J=20 Hz), 7.03–7.19 (2H, m), 7.37 (1H, t, J=8 Hz), 8.14 (1H, d, J=8 Hz)

EXAMPLE 62

Disodium salt of
[N-(3,4-dichlorophenyl)thiocarbamoylmethylene]bis(phosphonic acid)

mp: 248°–250° C. (dec.)
IR (Nujol): 3700–2300 (br), 1190, 1090 cm$^{-1}$
NMR (D$_2$O, δ): 4.03 (1H, t, J=20 Hz), 7.53–7.64 (2H, m), 8.03 (1H, s)

EXAMPLE 63

Disodium salt of
[N-(2-pyridyl)carbamoylmethylene]bis(phosphonic acid)

mp: >300° C.
IR (Nujol): 3700–2100 (br), 1675 cm$^{-1}$
NMR (D$_2$O, δ): 3.47 (1H, t, J=20 Hz), 7.27 (1H, t, J=6 Hz), 7.83 (1H, d, J=8 Hz), 7.95 (1H, t, J=8 Hz), 8.29 (1H, d, J=6 Hz)

EXAMPLE 64

Disodium salt of
[N-(2-benzo[b]thienyl)-thiocarbamoylmethylene]bis(phosphonic acid)

mp: >280° C.
IR (Nujol): 3700–2300 (br), 1460, 1410, 1230, 1160 cm$^{-1}$
NMR (D$_2$O, δ): 4.02 (1H, t, J=20 Hz), 7.35–7.47 (2H, m), 7.45 (1H, s), 7.85 (1H, d, J=11 Hz), 7.97 (1H, d, J=15 Hz)

EXAMPLE 65

Disodium salt of
[N-(2-trifluoromethylphenyl)thiocarbamoylmethylene]bis(phosphonic acid)

mp: 212° C. (dec.)
IR (Nujol): 3250, 2400, 1530, 1410, 1320, 1150, 1060 cm$^{-1}$
NMR (D$_2$O, δ): 4.16 (1H, t, J=21 Hz), 7.52–7.60 (1H, m), 7.65–7.76 (2H, m), 7.83 (1H, d, J=8 Hz)

EXAMPLE 66

Disodium salt of
[N-(4-chloro-3-trifluoromethylphenyl)thiocarbamoylmethylene]bis(phosphonic acid)

mp: 245° C. (dec.)
IR (Nujol): 3350, 3200, 1620, 1560, 1485, 1415, 1320 cm$^{-1}$
NMR (D$_2$O, δ): 4.00 (1H, t, J=20 Hz), 7.68 (1H, d, J=9 Hz), 7.88 (1H, d, J=9 Hz), 8.29 (1H, s)

EXAMPLE 67

Disodium salt of
[N-(4-methoxy-3-trifluoromethylphenyl)thiocarbamoylmethylene]bis(phosphonic acid)

mp: 249°–252° C. (dec.)
IR (Nujol): 3250, 2350, 1505, 1325, 1280, 1130 cm$^{-1}$
NMR (D$_2$O, δ): 4.05.(1H, t, J=20 Hz), 7.28 (1H, d, J=9 Hz), 7.77 (1H, d, J=9 Hz), 7.97 (1H, d, J=2 Hz)

EXAMPLE 68

Disodium salt of
[N-(n-butyl)thiocarbamoylmethylene]bis(phosphonic acid)

mp: >250° C.
(Nujol): 3500, 3250, 1560, 1280, 1180, 1065 cm$^{-1}$
NMR (D$_2$O, δ): 0.94 (3H, t, J=7 Hz), 1.33–1.51 (2H, m), 1.51–1.69 (2H, m), 3.61 (2H, t, J=8 Hz), 3.91 (1H, t, J=21 Hz)

EXAMPLE 69

Disodium salt of
[N-(4-trifluoromethylphenyl)carbamoylmethylene]bis(phosphonic acid)

mp: >250° C.
IR (Nujol): 3700–3000 (br), 2300, 1650, 1600, 1335, 1100 cm$^{-1}$
NMR (D$_2$O, δ): 3.31 (1H, t, J=20 Hz), 7.70 (4H, s)

EXAMPLE 70

Disodium salt of
[N-(4-methylthioplenyl)thiocarbamoylmethylene]bis(phosphonic arid)

mp: 215° C. (dec.)
IR (Nujol): 3500, 3300, 1500, 1390, 1170, 1065 cm$^{-1}$
NMR (D$_2$O, δ): 2.5 (1H, s), 4.09 (1H, t, J=21 Hz), 7.4 (2H, d, J=8.6 Hz), 7.59 (2H, d, J=8.6 Hz)

EXAMPLE 71

Disodium salt of
[N-(4-mesylaminophenyl)thiocarbamoylmethylene]-bis(phosphonic acid)

mp: 225° C. (dec.)
IR (Nujol): 3200, 2350, 1510, 1320, 1150 cm$^{-1}$
NMR (D$_2$O, δ): 3.12 (3H, s), 4.08 (1H, t, J=20 Hz), 7.34 and 7.65 (each 2H, d, J=9 Hz)

EXAMPLE 72

Disodium salt of [N-(3-mesylaminophenyl)thiocarbamoylmethylene]bis(phosphonic acid)

mp: 212° C. (dec.)
IR (Nujol): 3300, 2400, 1620, 1340, 1160, 1080 cm$^{-1}$
NMR (D$_2$O, δ): 3.12 (3H, s), 4.80 (1H, t, J=20 Hz), 7.22–7.25 (1H, br d, J=6 Hz), 7.45–7.49 (2H, m), 7.73 (1H, br s)

EXAMPLE 73

Disodium salt of
[N-(4-acetylaminophenyl)thiocarbamoylmethylene]-bis(phosphonic acid)

mp: 218° C. (dec.)

IR (Nujol): 3250, 2350, 1660, 1510, 1400, 1140, 1060 cm$^1$

NMR (D$_2$O, δ): 2.18 (3H, s), 4.80 (1H, t, J=20 Hz), 7.50 and 7.64 (2H, d, J=8 Hz)

EXAMPLE 74

Disodium salt of
[N-(3-acetylaminophenyl)thiocarbamoyl]methylenebis(phosphonic acid)

mp: 209° C. (dec.)

IR (Nujol): 3200, 2350, 1670, 1605, 1550, 1160, 1080 cm$^{-1}$

NMR (D$_2$O, δ): 2.16 (3H, s), 4.80 (1H, t, J=20 Hz), 7.35–7.57 (2H, m), 7.76 (1H, br s)

EXAMPLE 75

Tris(tert-butylamine) salt of [N-(phenyl)-thiocarbamoylmethylene]bis(phosphonic acid) (9.07 g) was passed through the column chromatography on Dowex 50W×8 (H$^+$, 76 ml) with water and the eluents were concentrated to give the residue containing [N-(phenyl)thiocarbamoylmethylene]bis(phosphonic acid). To 1M aqueous solution of sodium acetate (34.2 ml) was added the solution of the obtained residue in water (34.2 ml) and the mixture was stirred for 30 minutes. After ethanol (160 ml) was added thereto, the mixture was heated to give a precipitate. The mixture was cooled an the resulting precipitate was collected by filtration to give disodium salt of [N-(phenyl)thiocarbamoylmethylene]bis(phosphonic acid) (6.07 g).

mp: 216° C. (dec.)

IR (Nujol): 3500, 3300, 1505, 1175, 1145, 920 cm$^{-1}$

NMR (D$_2$O, δ): 4.10 (1H, t, J=21 Hz), 7.3–7.75 (5H, m)

EXAMPLE 76

To a solution of tetraethyl [(2-benzo[b]thiophenecarboxamido)methylene]bis(phosphonate) (463 mg) in methylene chloride (2 ml) was added iodotrimethylsilane (1 ml) in one portion at 5° C. The mixture was stirred for one hour at 5° C., allowed to stand for 2 days in a refrigerator and then additionally stirred for one hour at ambient temperature. The mixture was extracted with water. The aqueous layer was washed with methylene chloride and diethyl ether and then evaporated under reduced pressure. The residue was dissolved in water and therein tert-butylamine (183 mg) was added. The mixture was lyophilized to give bis(-tert-butylamine)-salt of [(2-benzo[b]thiophenecarboxamido)methylene]bis(phosphonic acid) (277 mg) as a white powder.

mp: 234°–238° C.

IR (Nujol): 3700–2050 (br), 1640 cm$^{-1}$

NMR (D$_2$O, δ): 1.40 (18H, s), 4.59 (1H, t, J=20 Hz), 7.43–7.58 (2H, m), 7.95–8.08 (2H, m), 8.11 (1H, s)

EXAMPLE 77

Tris(tert-butylamine)salt of [2-quinolinecarboxamido)methylene]bis (phosphonic acid) was obtained according to a similar manner to that of Example 76.

IR (Nujol): 3700–2000 (br), 1660 cm$^{-1}$

NMR (D$_2$O, δ): 1.46 (27H, s), 4.61 (1H, t, J=20 Hz), 7.76 (1H, t, J=11 Hz), 7.94 (1H, t, J=11 Hz), 8.08 (1H, d, J=8 Hz), 8.20 (2H, t, J=11 Hz), 8.58 (1H, d, J=8 Hz)

EXAMPLE 78

[(2-Pyridinecarboxamido)methylene]bis(phosphonic acid) was obtained according to a similar manner to that of Example 76.

mp: 277° C. (dec.)

IR (Nujol): 3150, 1670, 1640, 1615 cm$^{-1}$

NMR (DMSO-d$_6$, δ): 4.60 (1H, td, J=20 and 10 Hz), 7.63–7.70 (1H, m), 8.00–8.10 (1H, m), 8.37 (1H, d, J=10 Hz), 8.70 (1H, br d, J=5 Hz)

A mixture of [(2-pyridinecarboxamido)methylene]bis(phosphonic acid) (180 mg) and sodium acetate trihydrate (165 mg) in water (2 ml) was stirred for 30 minutes at ambient temperature, and then filtered. Ethanol (6 ml) was added to the filtrate to give a suspension. This suspension was heated and insoluble material was filtered off. The filtrate was allowed to stand and the precipitate was collected to give disodium salt of [(2pyridinecarboxamido)methylene]bis(phosphonic acid) (131 mg) as a white powder.

mp: >300° C.

IR (Nujol): 3700–2300 (br), 1670 cm$^{-1}$

NMR (D$_2$O, δ): 4.64 (1H, t, J=20 Hz), 7.64–7.71 (1H, m), 8.04–8.14 (2H, m), 8.66 (1H, d, J=5 Hz)

The following compounds (Examples 79 and 80) were obtained according to a similar manner to that of Example 78.

EXAMPLE 79

Disodium salt of
(benzoylaminomethylene)bis(phosphonic acid)

mp: >260° C.

NMR (D$_2$O, δ): 4.66 (1H, t, J=20 Hz), 7.20–7.50 (3H, m), 7.85 (2H, d, J=8 Hz)

EXAMPLE 80

Disodium salt of
[(4-chlorobenzoylamino)methylene]bis(phosphonic acid)

mp: >260° C.

NMR (D$_2$O, δ): 4.65 (1H, t, J=20 Hz), 7.55 (2H, d, J=9 Hz), 7.83 (2H, d, J=9 Hz)

EXAMPLE 81

To a solution of tetraethyl [[2-{1-(tert-butoxycarbonyl)imidazol-4-yl}acetamido]methylene]bis(phosphonate) (67 mg) in methylene chloride (1 ml) was added iodotrimethylsilane (0.12 ml) dropwise with stirring on an ice-water bath under nitrogen atmosphere. The mixture was stirred for 1 hour under the same condition and then for 2 hours at ambient temperature. After added water (1 ml) with stirring under ice-cooling, the mixture was stirred for 15 minutes. To the mixture were added water (4 ml) and chloroform (4 ml). The separated aqueous layer was washed with chloroform (5 ml) four times and concentrated under reduced pressure to give a yellow syrup (70 mg).

The syrup was dissolved in water (0.5 ml) and stirred for 3 hours at ambient temperature to give a white precipitate. The precipitate was filtered and washed with cold water (1 ml) to give a white powder of [{2-(imidazol-4-yl)acetamido}methylene]bis(phosphonic acid) (20 mg).

mp: 247°-250° C.

NMR (D$_2$O, δ): 3.77 (2H, s), 4.55 (1H, t, J=21 Hz), 7.24 (1H, s), 8.51 (1H, s)

EXAMPLE 82

To a solution of tetraethyl (phenylsulfonylaminomethylene)bis(phosphonate) (400 mg) in methylene chloride (4 ml), was added iodotrimethylsilane (0.8 ml) dropwise with stirring under nitrogen gas atmosphere in an ice-water bath. The mixture was stirred for 30 minutes at the same condition and then at ambient temperature for 1.5 hours. To the reaction mixture were added water (10 ml) and chloroform (8 ml) under ice-water bath cooling. The separated aqueous layer was washed with chloroform until its color disappeared and then evaporated in reduced pressure. The residue was washed with ethanol to give white powder of (phenylsulfonylaminomethylene)bis(phosphonic acid) (194 mg).

mp: 215°-216° C.

NMR (D$_2$O, δ): 3.95 (1H, t, J=21 Hz), 7.50-7.70 (3H, m), 7.89 (1H, dd, J=1, 8 Hz)

The following compounds (Examples 83 to 86) were obtained according to a similar manner to that of Example 82.

EXAMPLE 83

(Tosylaminomethylene)bis(phosphonic acid)

mp: 232°-233° C.

NMR (D$_2$O, δ): 3.98 (1H, t, J=21 Hz), 7.78 and 7.41 (4H, ABq, J=8.1 Hz)

EXAMPLE 84

[(4-Chlorophenyl)sulfonylaminomethylene]bisphosphonic acid)

mp: 255°-256° C. (dec.)

NMR (D$_2$O, δ): 3.94 (1H, t, J=22 Hz), 7.60 (2H, d, J=8 Hz), 7.88 (2H, d, J=8 Hz)

Disodium salt of [(4-chlorophenyl)sulfonylaminomethylene]bis(phosphonic acid) was obtained according to a similar manner to that of Example 78 from [(4-chlorophenyl)sulfonylaminomethylene]bis(phosphonic acid) and sodium acetate trihydrate.

mp: >260° C.

NMR (D$_2$O, δ): 3.80 (1H, t, J=20 Hz), 7.59 (2H, d, J=8 Hz), 7.88 (2H, d, J=8 Hz)

EXAMPLE 85

[(3,4-Dichlorophenyl)sulfonylaminomethylene]bis(phosphonic acid)

mp: >250° C.

IR (Nujol): 3100, 1345, 1270, 1230, 1050 cm$^{-1}$

NMR (D$_2$O, δ): 3.74 (1H, t, J=20 Hz), 7.70 (1H, d, J=9 Hz), 7.80 (1H, d, J=9 Hz), 8.09 (1H, s)

EXAMPLE 86

[(2-Thienyl)sulfonylaminomethylene]bis(phosphonic acid)

mp: 231° C. (dec.)

IR (Nujol): 3540, 1325, 1165 cm$^{-1}$

NMR (D$_2$O, δ): 3.98 (1H, t, J=21 Hz), 7.1-7.2 (1H, m), 7.73 (1H, d, J=3.5 Hz), 7.79 (1H, d, J=5 Hz)

EXAMPLE 87

Disodium salt of [(8-quinolyl)sulfonylaminomethylene]bis(phosphonic acid) was obtained according to a similar manner to that of Example 84.

mp: >260° C.

NMR (D$_2$O, δ): 3.65 (1H, t, J=19 Hz), 7.61 (1H, dd, J=3, 7 Hz), 7.65 (1H, t, J=7 Hz), 8.11 (1H, d, J=7 Hz), 8.40 (1H, d, J=7 Hz), 8.44 (1H, d, J=7 Hz), 8.96 (1H, d, J=3 Hz)

What we claim is:

1. A compound of the formula:

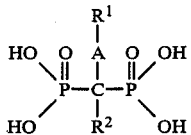

wherein

R$^1$—A— is a group of the formula:

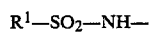

in which

R$^1$ is phenyl, naphthyl, pyridyl, imidazolyl, thienyl, quinolyl, benzothienyl or benzothiazolyl, unsubstituted or substituted with a substituent selected from the group consisting of lower alkyl, lower alkoxy, lower alkylthio, halo(lower) alkyl, lower alkoxycarbonyl, lower alkanoylamino, lower alkylsulfonylamino and halogen, and R$^2$ is hydrogen or lower alkyl, or a pharmaceutically acceptable salt thereof.

2. A bone-resorption inhibitory pharmaceutical composition comprising, as an active ingredient, an effective amount of a compound of claim 1 or pharmaceutically acceptable salt thereof in association with a pharmaceutical carrier.

3. A method for the treatment of bone diseases having abnormal bone metabolism in human beings or animals comprising administering an effective amount of a compound of claim 1 or pharmaceutically acceptable salt thereof.

* * * * *